(12) United States Patent
Deane

(10) Patent No.: US 12,708,462 B2
(45) Date of Patent: Aug. 18, 2026

(54) POWERING A SURGICAL ROBOT ARM

(71) Applicant: CMR SURGICAL LIMITED, Cambridge (GB)

(72) Inventor: Gordon Thomas Deane, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 153 days.

(21) Appl. No.: 17/919,886

(22) PCT Filed: Apr. 21, 2021

(86) PCT No.: PCT/GB2021/050951

§ 371 (c)(1),
(2) Date: Oct. 19, 2022

(87) PCT Pub. No.: WO2021/214454

PCT Pub. Date: Oct. 28, 2021

(65) Prior Publication Data

US 2023/0165644 A1 Jun. 1, 2023

(30) Foreign Application Priority Data

Apr. 24, 2020 (GB) ..................................... 2006043

(51) Int. Cl.
*A61B 34/30* (2016.01)
*A61B 1/00* (2006.01)

(52) U.S. Cl.
CPC ............ *A61B 34/30* (2016.02); *A61B 1/0016* (2013.01); *A61B 2034/302* (2016.02); *A61B 2034/305* (2016.02)

(58) Field of Classification Search
CPC . A61B 34/30; A61B 1/0016; A61B 2034/302; A61B 2034/305; A61B 2090/5025; A61B 1/00149; A61B 34/25
See application file for complete search history.

(56) References Cited

U.S. PATENT DOCUMENTS 10,258,416 B2 4/2019 Mintz et al.
2006/0087746 A1 4/2006 Lipow
(Continued)

FOREIGN PATENT DOCUMENTS

EP 3120979 A1 1/2017
EP 3733108 A1 11/2020
(Continued)

OTHER PUBLICATIONS

Japanese Notification of Reason for Rejection from corresponding Japanese Patent Application No. 2022-564410 dated Sep. 29, 2023.
(Continued)

*Primary Examiner* — Adam R Mott
*Assistant Examiner* — Sagar KC
(74) *Attorney, Agent, or Firm* — Lando & Anastasi, LLP

(57) ABSTRACT

A surgical robot comprising: a surgical robot arm comprising: a series of joints extending from a base to a terminal end for attaching to a surgical instrument for inserting through a port into a patients body to a surgical site, the series of joints comprising a first set of joints, wherein for each joint of the first set of joints, there is a configuration of the surgical robot arm for which that joint experiences a gravitational torque or force and a movement of that joint complying with the gravitational torque or force would cause the surgical instrument to advance into the patients body towards the surgical site; and joint motors for driving the series of joints; and a robot arm controller configured to send drive signals to drive the joint motors, wherein the surgical robot arm controller is configured to, in response to detecting a power loss, send drive signals to drive the joint motors so as to hold the position of each joint of the first set ofjoints against gravity, thereby preventing the surgical instrument from advancing into the patients body towards the surgical site due to
(Continued)

movement of one or more joints of the first set of joints under gravity.

19 Claims, 12 Drawing Sheets

(56) References Cited

U.S. PATENT DOCUMENTS

| | | | | |
|---|---|---|---|---|
| 2010/0069920 | A1* | 3/2010 | Naylor | A61B 34/71 606/130 |
| 2014/0171965 | A1 | 6/2014 | Loh et al. | |
| 2014/0195048 | A1 | 7/2014 | Moll et al. | |
| 2014/0330288 | A1* | 11/2014 | Date | A61B 34/37 606/130 |
| 2015/0031953 | A1 | 1/2015 | Atarot et al. | |
| 2016/0157943 | A1 | 6/2016 | Mintz et al. | |
| 2017/0007336 | A1* | 1/2017 | Tsuboi | B25J 9/1674 |
| 2018/0008359 | A1 | 1/2018 | Randle | |
| 2018/0049835 | A1 | 2/2018 | Shelton, IV | |
| 2018/0079090 | A1* | 3/2018 | Koenig | G01L 3/14 |
| 2019/0262090 | A1 | 8/2019 | Kukubo et al. | |
| 2019/0328468 | A1* | 10/2019 | Schena | A61B 34/37 |
| 2020/0253678 | A1 | 8/2020 | Hulford et al. | |
| 2020/0306997 | A1 | 10/2020 | Koenig et al. | |
| 2020/0405403 | A1 | 12/2020 | Shelton, IV et al. | |
| 2021/0354286 | A1* | 11/2021 | DiMaio | B25J 9/0084 |
| 2022/0410404 | A1 | 12/2022 | Ruiz Morales et al. | |

FOREIGN PATENT DOCUMENTS

| | | | |
|---|---|---|---|
| EP | 2845546 | B1 | 5/2022 |
| GB | 2534558 | A | 8/2016 |
| JP | H07194610 | A | 8/1995 |
| JP | 2003127076 | A | 5/2003 |
| JP | 2003127085 | A | 5/2003 |
| JP | 2008544814 | A | 12/2008 |
| JP | 2014124229 | A | 7/2014 |
| JP | 2016152906 | A | 8/2016 |
| JP | 6290372 | B2 | 3/2018 |
| JP | 2019155116 | A | 9/2019 |
| JP | 2019534060 | A | 11/2019 |
| WO | 2007005555 | A2 | 1/2007 |
| WO | 2015137038 | A1 | 9/2015 |
| WO | 2018053349 | A1 | 3/2018 |
| WO | 2019128494 | A1 | 7/2019 |
| WO | 2019191561 | A1 | 10/2019 |

OTHER PUBLICATIONS

Japanese Office Action of the Decision of Rejection from corresponding Japanese Patent Application No. 2021-568151 dated Jun. 13, 2023.

Japanese Notification of Reason for Rejection from corresponding Japanese Patent Application No. 2021-567047 dated Dec. 2, 2022.

Japanese Notification of Reason for Rejection from corresponding Japanese Patent Application No. 2021-568151 dated Dec. 2, 2022.

Dibekci et al., Improving the Saftey of Medical Robotic Systems, 2018 7th IEEE International Conference on Biomedical, Robotics and Biomechatronics (Biorob), Enschede, The Netherlands, Aug. 26-29, 2018, pp. 73-78.

Notification of Transmittal of the International Search Report and the Written Opinion of the International Searching Authority from corresponding PCT/GB2021/050951 dated Jul. 27, 2021.

Notification of Transmittal of the International Search Report and the Written Opinion of the International Searching Authority from corresponding PCT/GB2021/050952 dated Jul. 27, 2021.

Notification of Transmittal of the International Search Report and the Written Opinion of the International Searching Authority from corresponding PCT/GB2021/050953 dated Jul. 29, 2021.

United Kingdom Search Report from corresponding United Kingdom Application No. 2006042.2 dated Oct. 14, 2020.

United Kingdom Search Report from corresponding United Kingdom Application No. 2006043.0 dated Oct. 14, 2020.

United Kingdom Search Report from corresponding United Kingdom Application No. 2006046.3 dated Oct. 8, 2020.

* cited by examiner

POWERING A SURGICAL ROBOT ARM

CROSS-REFERENCE TO RELATED APPLICATIONS

This application is a U.S. National Phase Application under 35 U.S.C. § 371 of International Application No. PCT/GB2021/050951, filed Apr. 21, 2021, which claims priority to United Kingdom Application No. 2006043.0, filed Apr. 24, 2020. Each application referenced above is hereby incorporated by reference in its entirety for all purposes.

BACKGROUND

It is known to use robots for assisting and performing surgery. FIG. 1 illustrates a typical surgical robotic system. A surgical robot 100 consists of a base 102, an arm 104 and an instrument 106. The base supports the robot, and may itself be attached rigidly to, for example, the operating theatre floor, the operating theatre ceiling or a cart. The arm extends between the base and the instrument. The arm is articulated by means of multiple flexible joints 108 along its length, which are used to locate the surgical instrument in a desired location relative to the patient. The surgical instrument is attached to the distal end of the robot arm. The surgical instrument penetrates the body of the patient at a port so as to access the surgical site. The surgical instrument comprises a shaft connected to a distal end effector 110 by a jointed articulation. The end effector engages in a surgical procedure. In FIG. 1, the illustrated end effector is a pair of jaws. A surgeon controls the surgical robot 100 via a remote surgeon console 112. The surgeon console comprises one or more surgeon input devices 114. These may take the form of a hand controller or foot pedal. The surgeon console also comprises a display 116.

A control system 118 connects the surgeon console 112 to the surgical robot 100. The control system receives inputs from the surgeon input device(s) and converts these to control signals to move the joints of the robot arm 104 and end effector 110. The control system sends these control signals to the robot. Joint controllers on the robot arm 104 drive the joints 108 to move accordingly.

Power for driving the joints of the robot arm 104 is provided to the robot arm from the surgeon console 112 via power cables. In the event of a power failure, it is known to use a mechanical brake to hold the joints of the robot arm 104 in position, and for the surgical instrument 106 to be removed from the patient manually.

SUMMARY OF THE INVENTION

According to an aspect of the invention, there is provided a surgical robot comprising: a surgical robot arm comprising: a series of joints extending from a base to a terminal end for attaching to a surgical instrument for inserting through a port into a patient's body to a surgical site, the series of joints comprising a first set of joints, wherein for each joint of the first set of joints, there is a configuration of the surgical robot arm for which that joint experiences a gravitational torque or force and a movement of that joint complying with the gravitational torque or force would cause the surgical instrument to advance into the patient's body towards the surgical site; and joint motors for driving the series of joints; and a robot arm controller configured to send drive signals to drive the joint motors, wherein the surgical robot arm controller is configured to, in response to detecting a power loss, send drive signals to drive the joint motors so as to hold the position of each joint of the first set of joints against gravity, thereby preventing the surgical instrument from advancing into the patient's body towards the surgical site due to movement of one or more joints of the first set of joints under gravity.

The series of joints may comprise a second set of joints, wherein for each joint of the second set of joints, there is no configuration of the surgical robot arm for which that joint experiences a gravitational torque or force.

Of the first and second sets of joints, the robot arm controller may be configured to only send drive signals to drive the joint motors so as to hold the position of the first set of joints against gravity in response to detecting a power loss.

The second set of joints may be adjacent to the base of the surgical robot arm.

The second set of joints may be between the base of the surgical robot arm and the first set of joints.

The series of joints may comprise a third set of joints, wherein for each joint of the third set of joints, there is a configuration of the surgical robot arm for which that joint experiences a gravitational torque or force but no movement of that joint alone complying with the gravitational torque or force would cause the surgical instrument to advance through the port towards the surgical site.

Of the first and third sets of joints, the robot arm controller may be configured to only send drive signals to drive the joint motors so as to hold the position of the first set of joints against gravity in response to detecting a power loss.

Of the first, second and third sets of joints, the robot arm controller may be configured to only send drive signals to drive the joint motors so as to hold the position of the first set of joints against gravity in response to detecting a power loss.

The third set of joints may be successive joints adjacent to the terminal end of the surgical robot arm.

The third set of joints may be between the terminal end of the surgical robot arm and the first set of joints.

The series of joints may consist of in order from the base of the surgical robot arm: a first roll joint, a first pitch joint, a second roll joint, a second pitch joint, a third roll joint, a third pitch joint, a first yaw joint, and a fourth roll joint.

The first set of joints may consist of the first pitch joint, the second roll joint and the second pitch joint.

The second set of joints may consist of the first roll joint.

The third set of joints may consist of the third roll joint, the third pitch joint, the first yaw joint, and the fourth roll joint.

The detected power loss may be loss of power to the surgical robot arm from a back-up battery supply.

The robot arm controller may be configured to detect a loss of power to the surgical robot arm from a primary power supply prior to detecting the loss of power to the surgical robot arm from the back-up battery supply.

The robot arm controller may be configured to, prior to detecting the loss of power from the primary power supply, control the surgical robot arm and attached surgical instrument to move according to inputs received from a remote surgeon input device.

The robot arm controller may be integrated into the surgical robot arm.

The surgical robot arm may be mounted on a support structure, and the robot arm controller may be integrated into the support structure.

According to an aspect of the invention, there is provided a control method for controlling a surgical robot arm comprising a series of joints extending from a base to a terminal end for attaching to a surgical instrument for inserting into a patient's body to a surgical site, the series of joints comprising a first set of joints, wherein for each joint of the first set of joints, there is a configuration of the surgical robot arm for which that joint experiences a gravitational torque or force and a movement of that joint complying with the gravitational torque or force would cause the surgical instrument to advance into the patient's body towards the surgical site, the surgical robot arm further comprising joint motors for driving the series of joints, the method comprising: sending drive signals to drive the joint motors, wherein the surgical robot arm controller is configured to, in response to detecting a power loss, send drive signals to drive the joint motors so as to hold the position of each joint of the first set of joints against gravity, thereby preventing the surgical instrument from advancing into the patient's body towards the surgical site due to movement of one or more joints of the first set of joints under gravity.

BRIEF DESCRIPTION OF THE FIGURES

The present invention will now be described by way of example with reference to the accompanying drawings. In the drawings.

DETAILED DESCRIPTION

Figure 1:
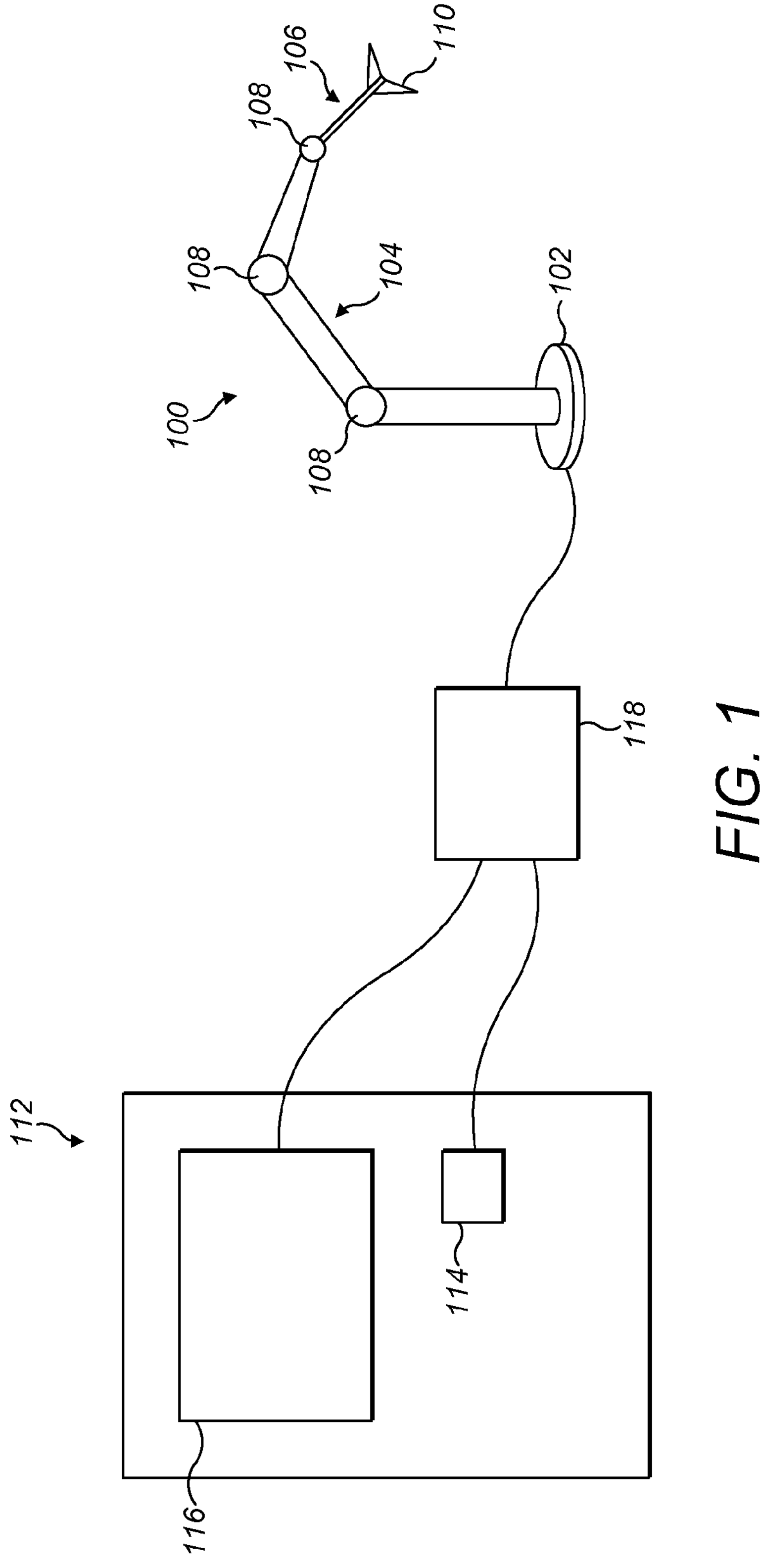
FIG. 1 illustrates a surgical robotic system for performing a surgical procedure.

The following describes a surgical robotic system of the type illustrated in FIG. 1. The surgical robotic system comprises one or more surgical robot arm and surgical instrument, along with a remote surgeon console. The remote surgeon console is connected to the surgical robot arm(s) via a control system. The control system includes a central controller located remotely from the surgical robot arm(s). The control system may also include a robot arm controller per surgical robot arm co-located with that surgical robot arm.

The control system and methods described in the following are done so with respect to a surgical robot arm holding a surgical instrument having an end effector at its distal end for manipulating tissue of a patient at a surgical site. The end effector may be, for example, a pair of jaws, scalpel, suturing needle etc. However, the same surgical robot arm, control system and methods apply equally to a surgical instrument which is an endoscope having a camera at its distal end for capturing a video feed of a surgical site.

Figure 2:
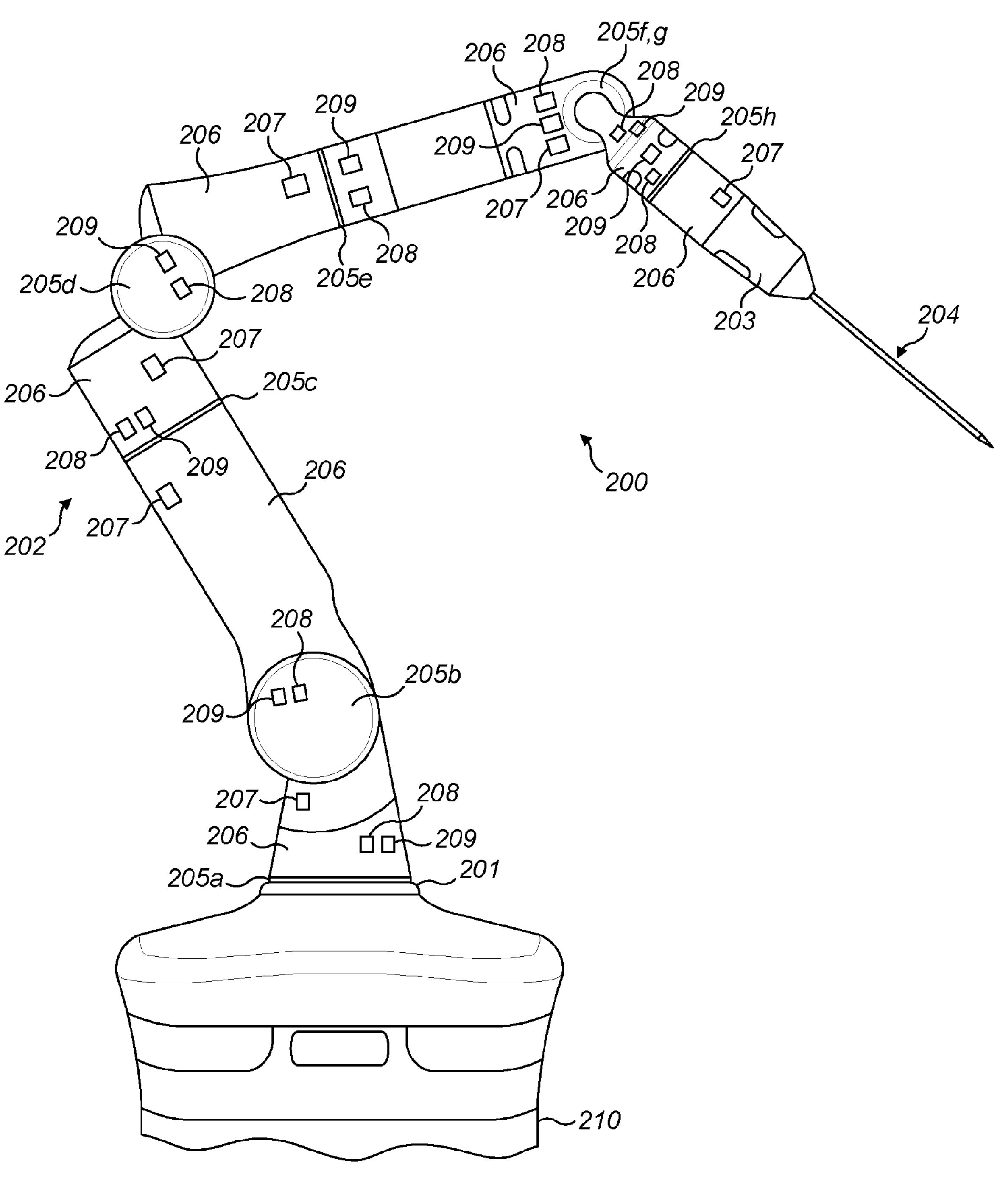
FIG. 2 illustrates a surgical robot arm.

FIG. 2 illustrates an exemplary surgical robot 200. The robot comprises a base 201 which is fixed in place when a surgical procedure is being performed. Suitably, the base 201 is mounted to a support structure. In FIG. 2, the support structure is a cart 210. This cart may be a bedside cart for mounting the robot at bed height. Alternatively, the support structure may be a ceiling mounted device, or a bed mounted device.

A robot arm 202 extends from the base 201 of the robot to a terminal end 203 for attaching to a surgical instrument 204. The arm is flexible. It is articulated by means of multiple flexible joints 205 along its length. In between the joints are rigid arm links 206. Suitably, the joints are revolute joints. The robot arm has at least seven joints between the base and the terminal end. The robot arm 200 illustrated in FIG. 2 has eight joints in total between the base 201 and the terminal end 203. The robot arm illustrated in FIG. 2 has only eight joints between the base and the terminal end. The joints include one or more roll joints (which have an axis of rotation along the longitudinal direction of the arm links on either side of the joint), one or more pitch joints (which have an axis of rotation transverse to the longitudinal direction of the preceding arm link), and one or more yaw joints (which also have an axis of rotation transverse to the longitudinal direction of the preceding arm link and also transverse to the rotation axis of a co-located pitch joint). In the example of FIG. 2: joints 205*a*, 205*c*, 205*e* and 205*h* are roll joints; joints 205*b*, 205*d* and 205*f* are pitch joints; and joint $\mathbf{205}_g$ is a yaw joint. The order of the joints sequentially from the base 201 of the robot arm to the terminal end 203 of the robot arm is: roll, pitch, roll, pitch, roll, pitch, yaw, roll. There are no intervening joints in FIG. 2.

Figure 3:
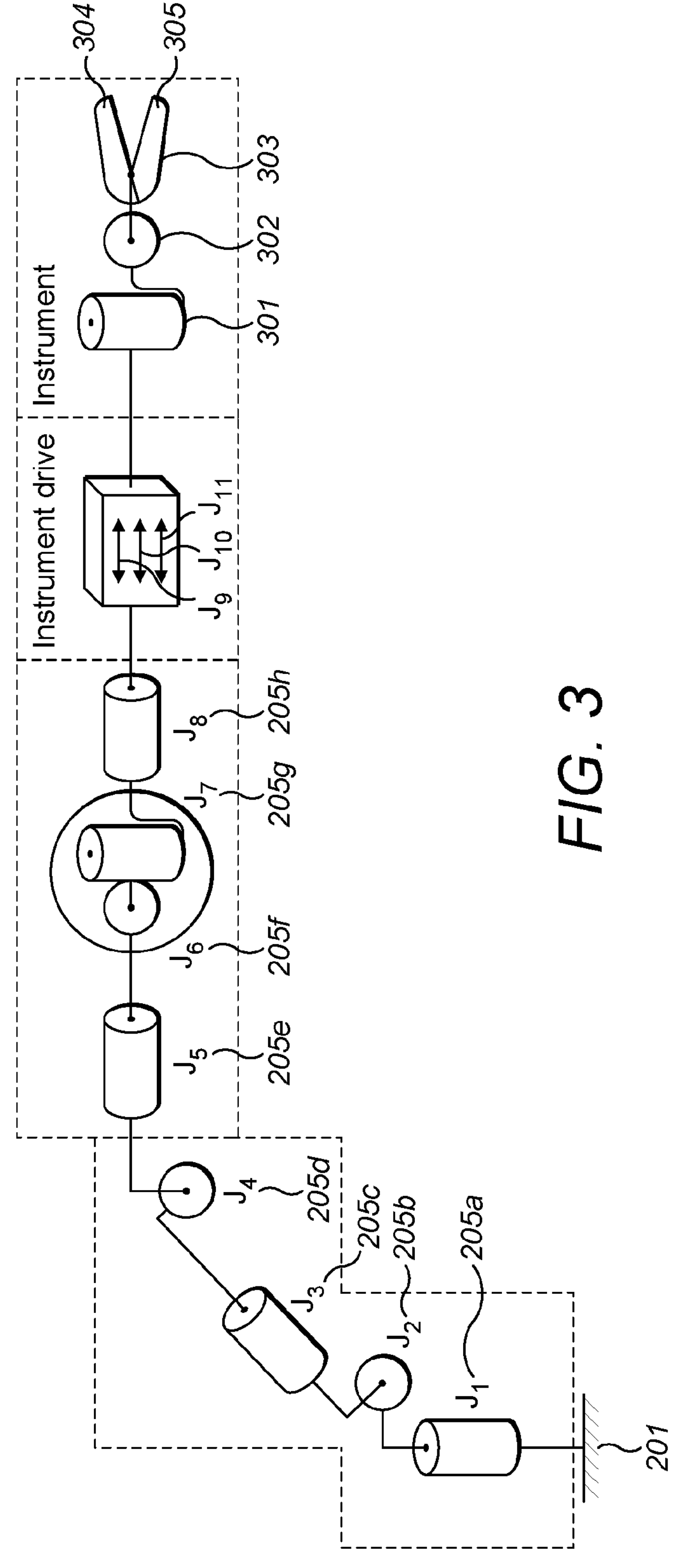
FIG. 3 illustrates an exploded view of the joints of the surgical robot arm of FIG. 2.

The joints of the surgical robot arm of FIG. 2 are illustrated on FIG. 3. The robot arm is articulated by eight joints. Roll joint $J_1$ 205*a* is adjacent to the base 201, and is followed by a pitch joint $J_2$ 205*b*. The pitch joint $J_2$ has a rotation axis perpendicular to the rotation axis of the roll joint $J_1$. Roll joint $J_3$ 205*c* is adjacent to the pitch joint $J_2$, and is followed by a pitch joint $J_4$ 205*d*. The pitch joint $J_4$ has a rotation axis perpendicular to the rotation axis of the roll joint $J_3$. Roll joint $J_5$ 205*e* is adjacent to the pitch joint $J_4$, and is followed by a pitch joint $J_6$ 205*f* and a yaw joint $J_7$ 205*g*, followed by a roll joint $J_8$ 205*h*. The pitch joint $J_6$ and yaw joint $J_7$form a compound joint, which may be a spherical joint. The pitch joint $J_6$ and the yaw joint $J_7$ have intersecting axes of rotation.

The end of the robot arm distal to the base can be articulated relative to the base by movement of one or more of the joints of the arm. The rotation axes of the set of distal joints $J_5$, $J_6$, $J_7$ and $J_8$ all intersect at a point on the surgical robot arm. Reference is made to a wrist. Suitably, the wrist is a portion of the robot arm which rigidly couples to the distal end of an instrument when that instrument is attached to the robot arm. The wrist has a position and an orientation. For example, the position of the wrist may be the intersection of the rotation axes of $J_5$, $J_6$, $J_7$ and is Alternatively, the position of the wrist may be the intersection of one or more rotation axes of joints of the instrument. Alternatively, the position of the wrist may be the intersection of one or more rotation axes of the distal joints of the robot arm and one or more rotation axes of joints of the instrument. The surgical robot arm illustrated in FIGS. 2 and 3 has a redundant joint. For a given position of the wrist relative to the base of the surgical robot arm, there is more than one configuration of the joints $J_1$ to $J_4$. Thus, the surgical robot arm can adopt different poses whilst maintaining the same wrist position.

The surgical robot arm could be jointed differently to that illustrated in FIGS. 2 and 3. For example, the arm may have fewer than eight or more than eight joints. The arm may include joints that permit motion other than rotation between respective sides of the joint, for example a telescopic joint.

Returning to FIG. 2, the surgical robot arm comprises a set of motors 207. Each motor 207 drives one or more of the joints 205. Each motor 207 is controlled by a joint controller.

The joint controller may be co-located with the motor 207. A joint controller may control one or more of the motors 207. The robot arm comprises a series of sensors 208, 209. These sensors comprise, for each joint, a position sensor 208 for sensing the position of the joint, and a torque sensor 209 for sensing the applied torque about the joint's rotation axis. The torque applied about a joint's rotation axis includes any one or combination of the following components: torque due to gravity acting on the joint, torque due to inertia, and torque due to an external force applied to the joint. One or both of the position and torque sensors for a joint may be integrated with the motor for that joint. The outputs of the sensors are passed to the control system.

The surgical instrument 204 attaches to a drive assembly at the terminal end of the robot arm 203. This attachment point is at all times external to the patient. The surgical instrument 204 has an elongate profile, with a shaft spanning between its proximal end which attaches to the robot arm and its distal end which accesses the surgical site within the patient's body. The surgical instrument may be configured to extend linearly parallel with the rotation axis of the joint 205*h* of the arm. For example, the surgical instrument may extend along an axis coincident with the rotation axis of the joint 205*h* of the arm.

The proximal end of the surgical instrument and the instrument shaft may be rigid with respect to each other and rigid with respect to the distal end of the robot arm when attached to it. An incision is made into the patient's body, through which a port is inserted. The surgical instrument may penetrate the patient's body through the port to access the surgical site. Alternatively, the surgical instrument may penetrate the body through a natural orifice of the body to access the surgical site. At the proximal end of the instrument, the shaft is connected to an instrument interface. The instrument interface engages with the drive assembly at the distal end of the robot arm. Specifically, individual instrument interface elements of the instrument interface each engage a respective individual drive assembly interface element of the drive assembly. The instrument interface is releasably engageable with the drive assembly. The instrument can be detached from the robot arm manually without requiring any tools. This enables the instrument to be detached from the drive assembly quickly and another instrument attached during an operation.

At the distal end of the surgical instrument, the distal end of the instrument shaft is connected to an end effector by an articulated coupling. The end effector engages in a surgical procedure at the surgical site. The end effector may be, for example, a pair of jaws, a pair of monopolar scissors, a needle holder, a fenestrated grasper, or a scalpel. The articulated coupling comprises several joints. These joints enable the pose of the end effector to be altered relative to the direction of the instrument shaft. The end effector itself may also comprise joints. The end effector illustrated in FIGS. 2 and 3 has a pair of opposing end effector elements 307, 308. The joints of the end effector are illustrated on FIG. 3 as a pitch joint 301, a yaw joint 302 and a pinch joint 303. The pitch joint 301 is adjacent to the shaft of the instrument and rotates about an axis perpendicular to the longitudinal axis of the instrument shaft. The yaw joint 302 has a rotation axis perpendicular to the rotation axis of the pitch joint 301. The pinch joint 303 determines the spread of the end effector elements. In practice, the pinch joint 303 may be another yaw joint which has the same rotation axis as the yaw joint 302. Independent operation of the two yaw joints 302, 303 can cause the end effector elements to yaw in unison, and/or to open and close with respect to each other.

Drive is transmitted from the robot arm to the end effector in any suitable manner. For example, the joints of the instrument may be driven by driving elements such as cables, push rods or push/pull rods. These driving elements engage the instrument interface at the proximal end of the instrument. The drive assembly at the terminal end of the robot arm comprises instrument drive joints which transfer drive from the surgical robot arm to the instrument interface via the respective interface elements described above, and thereby to the instrument joints. These instrument drive joints are shown on FIG. 3 as joints $J_9$, $J_{10}$ and $J_{11}$. FIG. 3 illustrates three instrument drive joints, each one of which drives one of the three joints of the instrument.

Suitably, the instrument drive joints are the only means by which drive is transferred to the instrument joints. The robot arm may have more or fewer than three instrument drive joints. The surgical instrument may have more or fewer than three joints. The instrument drive joints may have a one-to-one mapping to the instrument joints that they drive, as shown in FIG. 3. Alternatively, an instrument drive joint may drive more than one instrument joint.

The surgeon console is located remotely from the one or more surgical robot arms of the surgical robotic system. The surgeon console comprises one or more surgeon input devices and a display. Each surgeon input device enables the surgeon to provide a control input to the control system. A surgeon input device may, for example, be a hand controller, a foot controller such as a pedal, a touch sensitive input to be controlled by a finger or another part of the body, a voice control input device, an eye control input device or a gesture control input device. The surgeon input device may provide several inputs which the surgeon can individually operate.

For example, the surgeon input device may be a hand controller connected to the surgeon console, for example by a gimbal arrangement. This enables the hand controller to be moved with three degrees of translational freedom with respect to the surgeon console. Such movement may be used to command corresponding movement of the end effector of the instrument. The hand controller may also be rotated with respect to the surgeon console. Such movement may be used to command corresponding rotation of the end effector of the instrument.

The surgeon console may comprise two or more surgeon input devices. Each surgeon input device may be used to control a different surgical instrument. Thus, for example, a surgeon may control one surgical instrument using a hand controller in his left hand, and control another surgical instrument using a hand controller in his right hand.

Figure 4:
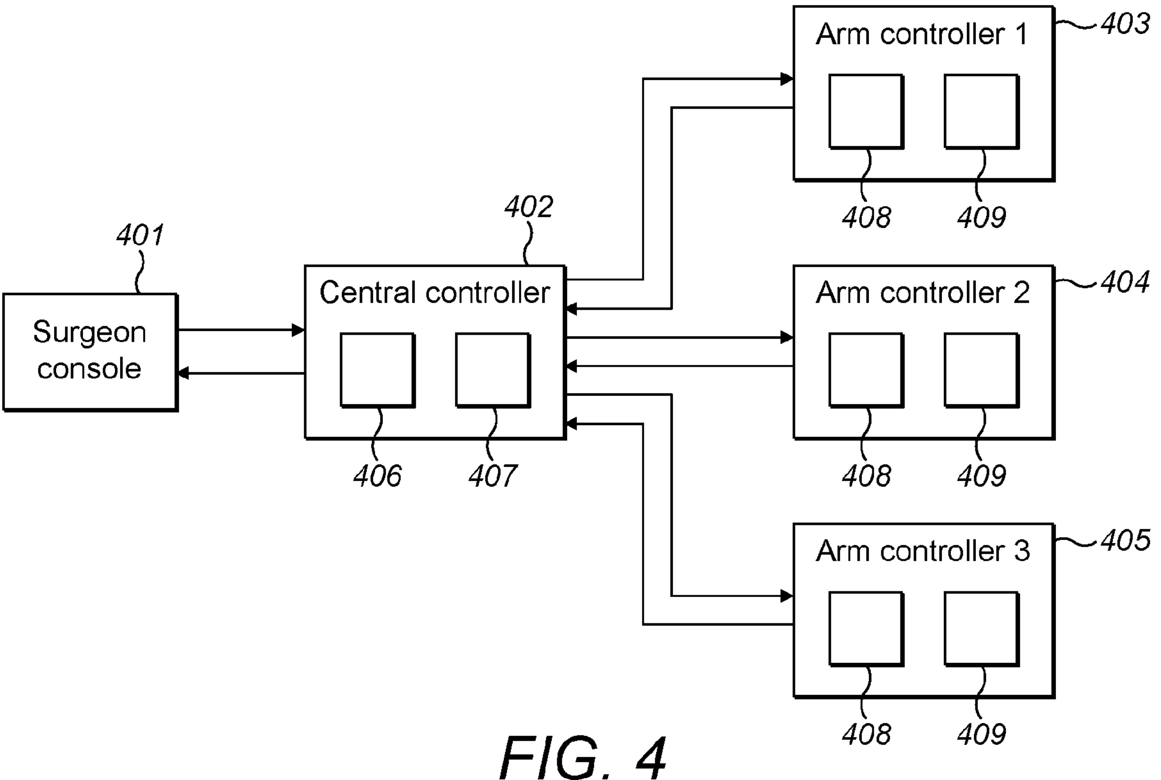
FIG. 4 is a schematic diagram illustrating the control system of a surgical robotic system.

A control system connects the surgeon console to the one or more surgical robots. Such a control system is illustrated in FIG. 4. The surgeon console 401 is connected by a bi-directional communications link to a central controller 402. Specifically, the surgeon input device(s) of the surgeon console 401 are communicatively coupled to the central controller 402. The central controller 402 is connected by a bi-directional communications link to an arm controller 403, 404, 405 of each surgical robot arm of the surgical robotic system. Each arm controller is co-located with a surgical robot arm. The arm controller may be located in the surgical robot arm. Alternatively, the arm controller may be located in the support structure which supports the surgical robot arm, for example in the cart of the arm. The central controller is remotely located from at least one of the surgical robot arms. Suitably, the central controller is remotely located from all the surgical robot arms in the surgical robotic system. The central controller may be located at the surgeon console. Alternatively, the central controller may be co-located with one of the arm controllers. The central controller may be located remote from both the surgeon console and all the arm controllers.

The central controller comprises a processor 406 and a memory 407. The memory 407 stores, in a non-transient way, software code that can be executed by the processor 406 to cause the processor to control the surgeon console and the one or more surgical robot arms and instruments in the manner described herein.

Each of the arm controllers comprises a processor 408 and a memory 409. The memory 409 stores, in a non-transient way, software code that can be executed by the processor 408 to cause the processor to control the surgeon console and the one or more surgical robot arms and instruments in the manner described herein.

The central controller 402 receives commands from the surgeon input device(s). The commands from the surgeon input device indicate a change in the desired position and/or pose of a distal end of a surgical instrument. The control system converts the commands received from the surgeon input device to drive signals. This conversion is carried out by one or a combination of the central controller and the surgical robot arm controller of the surgical robot arm associated with the surgeon input device. The robot arm controller sends the drive signals to the joint controllers of the surgical robot arm and/or surgical instrument associated with the surgeon input device. Those joint controllers respond by driving the joint motors accordingly. The joints are thereby driven to cause the end effector to adopt the desired position and/or pose commanded by the surgeon input device. Manipulation of the surgical instrument is thereby controlled by the control system in response to manipulation of the surgeon input device.

The control system receives inputs from the position and torque sensors on the joints of the surgical robot arms. The control system determines the current configuration of a surgical robot arm using the known sequence of joints and links in the arm, and the sensed joint positions. From the current configuration of the surgical robot arm and the attached surgical instrument, and the known mass and dimensions of the links and joints of the robot arm and instrument, the control system determines the torque due to gravity acting on each joint. The control system sends gravity compensating drive signals to the joint controllers of the robot arm. The joint controllers respond by driving the joint motors so as to counteract the force of gravity acting on each joint. In other words, each joint motor applies a torque which exactly opposes the calculated gravitational force acting on the joint. In the absence of commands from the surgeon input device and/or external forces (other than gravity) acting on the robot arm, the robot arm is thereby held in position against gravity. It does not droop under the force of gravity. In practice, each drive signal sent by the control system to a joint controller for driving a joint motor may be resolved into a component which drives the joint in accordance with the input received from the surgeon input device, and a component which counteracts gravity. In some modes, as discussed below, the drive signal may also comprise a component which drives the joint to conform with an external force applied to the robot arm.

Figure 5:
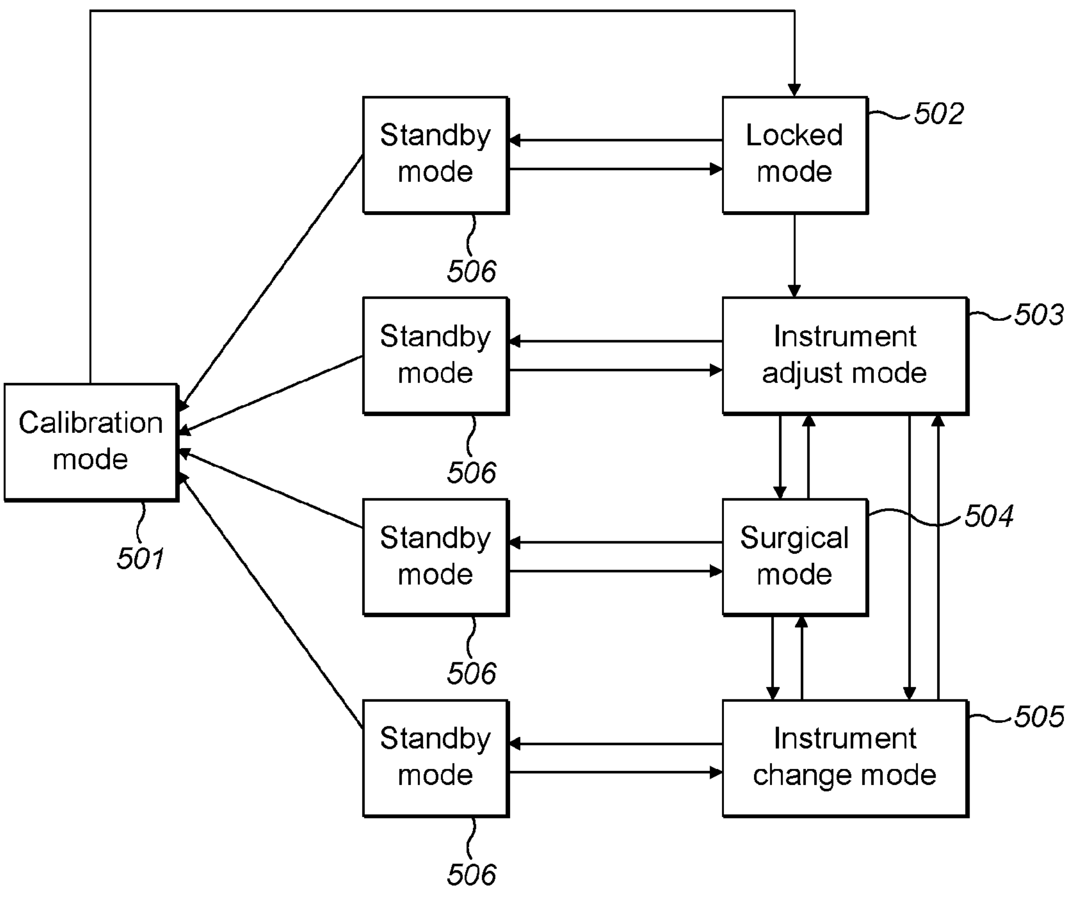
FIG. 5 illustrates operating modes of a surgical robot arm and the transitions permitted between them.

A surgical robot arm is operable in a number of different operating modes. FIG. 5 illustrates some exemplary operating modes of the surgical robot arm, and the transitions permitted between those operating modes.

FIG. 5 illustrates a calibration mode 501. In the calibration mode 501, the surgical robot arm is driven to conform to external forces applied to the robot arm. Specifically, the torque sensors 209 detect external forces applied to the robot arm. The external force may be, for example, a member of the bedside team applying a force to the robot arm (for example by pushing the robot arm). As described above, the sensed torque about a joint's rotation axis includes any one or combination of the following components: torque due to gravity acting on the joint, torque due to inertia, and torque due to an external force applied to the joint. The control system deducts the torques due to gravity and inertia from the sensed torque about a joint to determine the component of the torque about that joint due to an external force. The control system then determines drive signals to drive the joint so as to conform with the external force. The control system sends the drive signals to the joint controller controlling that joint. The joint controller controls the motor of that joint to drive the joint as commanded by the control system. In this way, when an external force is applied to a joint, that joint is driven to comply with that force. Thus, the robot arm is compliant to the force applied to it by an operator.

In the calibration mode 501, the control system drives the robot arm to oppose the gravitational torques acting on the robot arm as described above. Thus, in the calibration mode 501, a member of the bedside team can manoeuvre the robot arm into position by pushing or pulling any part of the robot arm in a desired position, and that part will stay in that position notwithstanding the effect of gravity on it and on any parts depending from it.

In the calibration mode 501, the control system does not convert detected manipulation of the surgeon input device(s) to drive signals for moving joints of the robot arm. Any inputs the control system receives from the surgeon input device are not converted to movement of the robot arm.

The calibration mode 501 is primarily used during setup of the surgical robotic system prior to the beginning of an operation. For example, a surgical instrument may be attached to the robot arm during the calibration mode 501 and a member of bedside staff may manoeuvre the robot arm so as to insert the surgical instrument into the port in the patient's body along the desired direction to reach the surgical site. Should a robot arm and its support structure be moved, or relocated during an operation, the calibration mode 501 is used again to manoeuvre the robot arm into position.

During setup of the surgical robotic system, the calibration mode is used to determine a virtual pivot point. The virtual pivot point is the natural centre of rotation of an instrument having a rigid shaft as that instrument moves in the patient's body. The virtual pivot point is a fulcrum about which the surgical instrument pivots when the configuration of the surgical robot arm is altered whilst inside the port in the patient's body. A port is inserted into the abdominal wall of the patient. The port is of the order of 2-10 cm long. The instrument is inserted into the patient's body through the port. The virtual pivot point lies along the length of the port. The exact location of the virtual pivot point depends on the patient's anatomy, and hence differs from patient to patient.

The virtual pivot point can be determined using the following method. With the instrument located in the port, an operator moves the distal end of the robot arm in directions generally transverse to the instrument shaft. This motion causes the port to exert a lateral force on the instrument shaft where it passes through the port, with the result that the instrument applies a torque to the joints of the arm—in this case joints $J_6$ 205*f* and $J_7$ 205$_g$—whose axes are transverse to the longitudinal axis of the instrument shaft. The position of each arm joint is measured by its associated position sensor 208, and this sensed position is output to the control system. The torque at each arm joint is measured by its associated torque sensor 209, and this sensed torque is output to the control system. Thus, as the operator moves the distal end of the robot arm laterally the control system receives sensed inputs indicating the position and forces on the arm joints. That information allows the control system to estimate: (a) the position of the distal end of the robot relative to the fixed base and (b) the vector of the instrument shaft relative to the distal end of the robot. Since the instrument shaft passes through the passageway of the port, the passageway of the port must lie along that vector.

As the distal end of the robot arm is moved, the controller calculates multiple pairs of distal end positions and instrument shaft vectors. Those vectors all converge, from their respective distal end position, on the location of the virtual pivot point in the passageway of the port. By collecting a series of those data pairs and then solving for the mean location where the instrument shaft vectors converge, the control system determines the virtual pivot point relative to the base.

Once the virtual pivot point is determined in the calibration mode 501, it is set for the remainder of the modes illustrated on FIG. 5. The virtual pivot point is stored by the control system. In each of the other modes illustrated in FIG. 5, the surgical robot arm is always driven such that the longitudinal axis of the shaft of the attached surgical instrument intersects the virtual pivot point (whether or not the instrument is actually attached to the robot arm). The longitudinal axis of the shaft of the surgical instrument has a known relationship to the longitudinal axis of the terminal end of the robot arm. For example, as shown in FIG. 2, the longitudinal axis of the shaft of the surgical instrument may be coincident with the longitudinal axis of the terminal end of the robot arm.

From the calibration mode, the surgical robot arm can transition to the locked mode 502. In the locked mode 502, the control system holds the surgical robot arm in a fixed position. That fixed position is the position that the surgical robot arm was in at the time that it transitioned from the calibration mode to the locked mode 502. In the locked mode, the control system drives the joints of the robot arm to compensate for gravity (as described above). Otherwise, the control system does not convert any manipulation of the surgeon input device or external forces applied to the robot arm to drive signals for driving the joints of the robot arm.

From the locked mode 502, the surgical robot arm can transition to the instrument adjust mode 503. In the instrument adjust mode 503, the control system drives the surgical robot arm to conform to external forces applied to the robot arm (as described above with respect to the calibration mode), whilst retaining the intersection of the longitudinal axis of the shaft of the surgical instrument with the virtual pivot point determined in the calibration mode. The instrument adjust mode 503 can be used to adjust the position of the instrument within the patient's body. For example, the instrument adjust mode 503 may be used to enable a member of the bedside team to push the instrument into the patient's body such that the end effector reaches the surgical site, following setting of the virtual pivot point in the calibration mode. In the instrument adjust mode 503, the control system drives the joints of the robot arm to compensate for gravity (as described above). In the instrument adjust mode 503, the control system does not convert any manipulation of the surgeon input device to drive signals for driving the joints of the robot arm.

From the instrument adjust mode 503, the surgical robot arm can transition to the surgical mode 504 or the instrument change mode 505. In the surgical mode 504, the control system responds to inputs received from a surgeon input device by converting those inputs to control signals for controlling the motion of the surgical robot arm and/or surgical instrument associated with that surgeon input device (as described above). The end effector of the surgical instrument thereby moves as commanded by the surgeon input device. When performing the conversion, the control system maintains an intersection between the longitudinal axis of the shaft of the surgical instrument and the virtual pivot point.

The surgical mode 504 may comprise a clutch mode. The clutch mode may be initiated by the surgeon console, for example via an input on the surgeon input device. Alternatively, the clutch mode may be initiated by an input on the surgical robot arm or the support to which the surgical robot arm is mounted. In the clutch mode, manipulation of the surgeon input device is temporarily disconnected from the robot arm. When receiving an input indicating that the clutch mode has been engaged, the control system does not convert manipulation of the surgeon input device to control signals for driving joints of the robot arm. The clutch mode is used by the surgeon in order to move the surgeon input device to a more comfortable location in the workspace of the surgeon input device without transferring that motion to the end effector of the surgical instrument. The clutch mode is also used by the surgeon to temporarily disengage one surgical instrument whilst the surgeon concentrates on a surgical instrument being manipulated by another surgeon input device.

The surgical mode 504 may be a semi-compliant mode. In other words, the robot arm may exhibit some compliant behaviour towards external force applied to the robot arm. For example, in the surgical mode 504, the control system may respond to a sensed external force applied proximal to the elbow joint **205*d* by controlling the motors driving the elbow joint 205*d* and the surrounding joints of the arm to drive those joints to comply with that sensed external force. In this way, a member of the bedside team can push the elbow joint 205*d* or a part of the arm proximal to the elbow joint out of the way to enable them to access the patient during the surgical mode. In order to implement this, the control system may define a permitted area/volume for one or more parts of the robot arm that are designated as compliant such that movement of those parts in response to externally applied forces is confined within the permitted area/volume. The permitted area/volume is defined such that movements within that area/volume in response to externally applied forces do not cause the configuration of the instrument to be affected. The robot arm is only semi-compliant in the surgical mode 504** because the control system does not respond by conforming to an external force applied to any part of the robot arm other than the parts designated as compliant.

From the surgical mode 504, the surgical robot arm can transition to the instrument adjust mode 503 or to the instrument change mode 505. The instrument change mode 505 is engaged in order to remove and/or insert the instrument from/into the patient's body. In the instrument change mode 505, the control system drives the surgical robot arm to conform to the component of a sensed external force applied to the robot arm along the longitudinal axis of the surgical instrument towards or away from the surgical robot arm. Whilst in the instrument change mode 505, the control system retains the intersection of the longitudinal axis of the shaft of the surgical instrument with the virtual pivot point determined in the calibration mode. The control system conforms to the sensed external force in the same manner as described above with respect to the calibration mode, the only differences being that (i) the control system only conforms to the component of the sensed force in the specified directions (i.e. along the longitudinal axis of the surgical instrument towards or away from the surgical robot arm), and (ii) the control system maintains intersection of the surgical instrument with the virtual pivot point.

At the end of an operation when surgical instruments are being removed from the surgical site, or mid-operation when a surgical instrument is being exchanged for another one, a member of the bedside team uses the instrument change mode 505 to enable them to pull the instrument out of the patient's body, and then insert another instrument into the patient's body. In the instrument change mode 505, the control system prevents force applied by the member of the bedside team in any direction other than the longitudinal axis of the surgical instrument towards or away from the surgical robot arm from being converted to corresponding movement of the surgical robot arm. Thus, no lateral force applied by the member of the bedside team is converted to corresponding movement of the surgical robot arm. This ensures that extraction of the surgical instrument is along the line of entry between the port and the surgical site, thus avoiding damage to tissue away from this line.

In the instrument change mode 505, the control system limits the conversion of force applied by the member of the bedside team along the longitudinal axis of the surgical instrument towards the patient's body to corresponding movement of the surgical robot arm. This limit is such that the end effector of the attached instrument cannot advance further into the patient's body than the end effector of the instrument at the time that the instrument change mode was entered. This limit applies to the same instrument that was attached to the arm at the time that the instrument change mode was entered during instrument extraction. This limit also applies to the newly attached instrument which is inserted into the patient's body following instrument change. This ensures that the surgical instrument cannot be pushed further into the patient's body causing damage to the surgical site.

In the instrument change mode 505, the control system drives the joints of the robot arm to compensate for gravity (as described above). In the instrument change mode 505, the control system does not convert any manipulation of the surgeon input device to drive signals for driving the joints of the robot arm.

From the instrument change mode 505, the surgical robot arm can transition to the instrument adjust mode 503 or the surgical mode 504.

From each of the locked mode 502, instrument adjust mode 503, surgical mode 504 and instrument change mode 505, the surgical robot arm can transition to a standby mode 506. From that standby mode 506, the surgical robot arm can transition back to the one of the locked mode, instrument adjust mode, surgical mode and instrument change mode that it was previously in. From the standby mode 506, the surgical robot arm can also transition to the calibration mode 501.

The surgical robot arm, or the support structure to which the robot arm is mounted, may comprise one or more interfaces. These interfaces may be a button or set of buttons. The interfaces can be actuated, for example by a member of the bedside team, to transition between the operating modes described with respect to FIG. 5. The surgeon's console may comprise one or more interfaces which can be actuated, for example by the surgeon, to transition between the operating modes described with respect to FIG. 5.

Power is required by the surgical robot arm to power the joint motors to drive the joints, as well as to power all the circuitry in the surgical robot arm including the robot arm controller and the joint controllers. The surgical robot arm is generally operated in a full power mode in which it is powered by a primary power source. This primary power source is sufficient to sustain the power requirements of the surgical robot arm throughout a surgical procedure. For example, the primary power source may be an electrical supply such as an electrical mains power supply. Power may be routed from the primary power source to the surgical robot arm through the surgeon's console.

The surgical robot arm may also be operable in a reduced power mode in which it is powered by a secondary power source. In this reduced power mode, fewer operating modes of the surgical robot arm are available for use. Referring to FIG. 5, the locked mode 502, instrument adjust mode 503, surgical mode 504 and instrument change mode 505 may only be available in the full power mode. They are not available in the reduced power mode. The calibration mode 501 and standby modes 506 may be fully available in the full power mode and partially or fully available in the reduced power mode.

The secondary power source may comprise one or more batteries. These batteries may be local to the surgical robot arm. For example, each of the one or more batteries may be located in the surgical robot arm itself, or in the support structure to which the surgical robot arm is mounted. The secondary power source may comprise two batteries. The first battery may be a rechargeable battery and the second battery may be a non-rechargeable battery. The first battery, when fully charged, can provide sufficient power to drive the motors of the surgical robot arm to hold the position of the surgical robot arm against gravity for at least N minutes. For example, $5<N<30$. For example, N=5. The second battery can provide sufficient power to drive motors of the surgical robot arm (as described below) to hold the surgical robot arm for at least T seconds. For example, $20<T<180$. For example, T=30. N and T are estimations of how long the batteries can provide the described power for. These estimations may be based on typical discharge v. time graphs for the batteries, or mathematical models of the ideal discharge of the batteries over time. The remaining battery life of each battery may be estimated by measuring the voltage, current or power output of the battery over time, and comparing those voltage/current/power readings against a typical battery life graph of voltage v. battery capacity. The maximum capacity of the first battery may be between 5000 and 6000 mAh. The maximum capacity of the second battery may be between 300 and 600 mAh.

A surgical robot arm may only be able to be powered up for use if it is connected to the primary power source in the full power mode. A robot arm controller on the surgical robot arm detects that sufficient power is being received from the primary power source to power the functions of the surgical robot arm. On detecting a power failure of the primary power source, the robot arm controller switches the surgical robot arm to the reduced power mode. In the reduced power mode, the robot arm controller controls the surgical robot arm to be powered from the secondary power source. For example, initially in the reduced power mode, the robot arm controller may control the surgical robot arm to be powered from the first battery. If the first battery becomes depleted, then the robot arm controller may control the surgical robot arm to be powered from the second battery. The robot arm controller may detect power failures, detect restoration of power following a power failure, and enable and disable the full power mode and the reduced power mode.

Control methods which may be carried out by the control system in response to detection of a power failure to a surgical robot arm are now explained with reference to FIGS. 6 to 12. Suitably, these control methods are performed by the robot arm controller of the surgical robot arm which has lost power.

Figure 6:
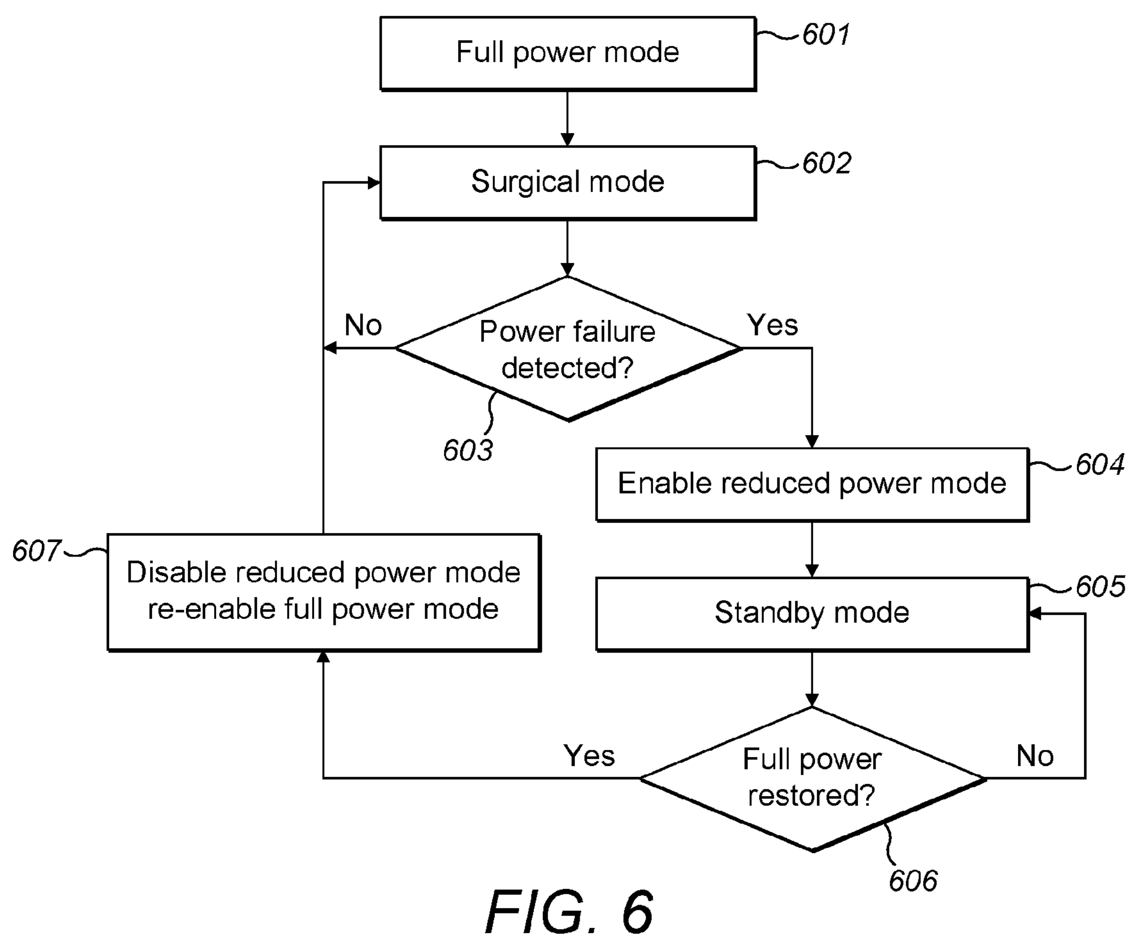
FIGS. 6, 7, 8, 9, 10, 11 and 12 are flowcharts illustrating control methods of a robot arm controller during a power failure.

Starting with FIG. 6, at step 601, the surgical robot arm is being operated in a full power mode with power being provided to the surgical robot arm by the primary power source. At step 602, the control system operates the surgical robot arm in surgical mode. At step 603, the control system determines whether a power failure to the surgical robot arm has been detected. If no power failure has been detected, the control system returns to step 602 where it continues to operate the surgical robot arm in the surgical mode. If a power failure has been detected at step 603, then the control system responds by enabling a reduced power mode at step 604 and entering a standby mode at step 605. The standby mode is a locked mode in which the control system sends control signals to the joint controllers of the robot arm commanding them to control the joint motors to drive the joints so as to hold the joints of the surgical robot arm locked in place. The control method then moves on to step 606, wherein it determines whether full power has been restored, i.e. whether the power failure has ceased. If the answer is NO, then the control system retains the surgical robot arm in the standby mode 605. If the answer is YES, then the control system moves to step 607. At step 607, the control system responds to detecting the cessation of the power failure by disabling the reduced power mode and re-enabling the full power mode. The control system then returns to the surgical mode 602.

Steps 604 and 605 could be implemented in the order shown in FIG. 6, the other way around, or concurrently. Step 607 could be implemented concurrently with a return to the surgical mode 602.

Although described with respect to the surgical mode, the method of FIG. 6 applies to any of the operating modes of the surgical robot arm described with respect to FIG. 5, i.e. the locked mode, instrument adjust mode and instrument change mode.

The control method of FIG. 6 is useful for surgical robot arms which do not have a mechanical brake, but are instead braked electrically. In the event of a loss of power from the primary power source, the control method of FIG. 6 ensures that the surgical robot arm is held locked in its current position in the standby mode. This prevents the surgical robot arm from drooping under gravity, which would otherwise happen if the robot arm is not powered to counteract the gravitational torques acting on the robot arm's joints. By holding the robot arm in position on a back-up battery supply, time is provided for restoring full power to the robot arm or removing the surgical instrument attached to the robot arm safely from the patient's body.

The control method of FIG. 6 aids in setting up the operating theatre for a procedure and tearing down the operating theatre after a procedure. Generally, several surgical robot arms and other equipment needs to be appropriately located around the patient's bedside and setup prior to a surgical operation commencing. The control method of FIG. 6 enables the power cable to a surgical robot arm to be intentionally unplugged, so as to enable other equipment to be wheeled past the surgical robot arm without having to be wheeled over the power cable. The power cable can then be re-plugged in, and the surgical robot arm returned to the operating mode it was previously in without having to re-perform any calibration procedures. During the time that the power cable is unplugged, the robot arm is held in position. The control method of FIG. 6 is also useful mid-operation to enable other components to be wheeled through the path of the power cable attached to the surgical robot arm.

In order for the surgical robot arm to return to the surgical mode once full power is restored, the virtual pivot point determined during the calibration mode is stored by the control system. The virtual pivot point continues to be stored by the control system during the reduced power mode. On returning to the surgical mode following the power failure, the virtual pivot point is retrieved from memory by the control system and used by the control system in determining the drive signals to send to the joint controllers to drive the joint motors of the robot arm. In this way, no re-calibration is required following the power failure. In order for no re-calibration to be required, the support structure of the surgical robot arm must remain stationary during the standby mode. If the support structure moves, for example by un-braking and re-braking the cart on which the robot arm is mounted, then the virtual pivot point will change. Hence the stored virtual pivot point will no longer be valid for use following restoration of full power to the surgical robot arm.

Figure 7:
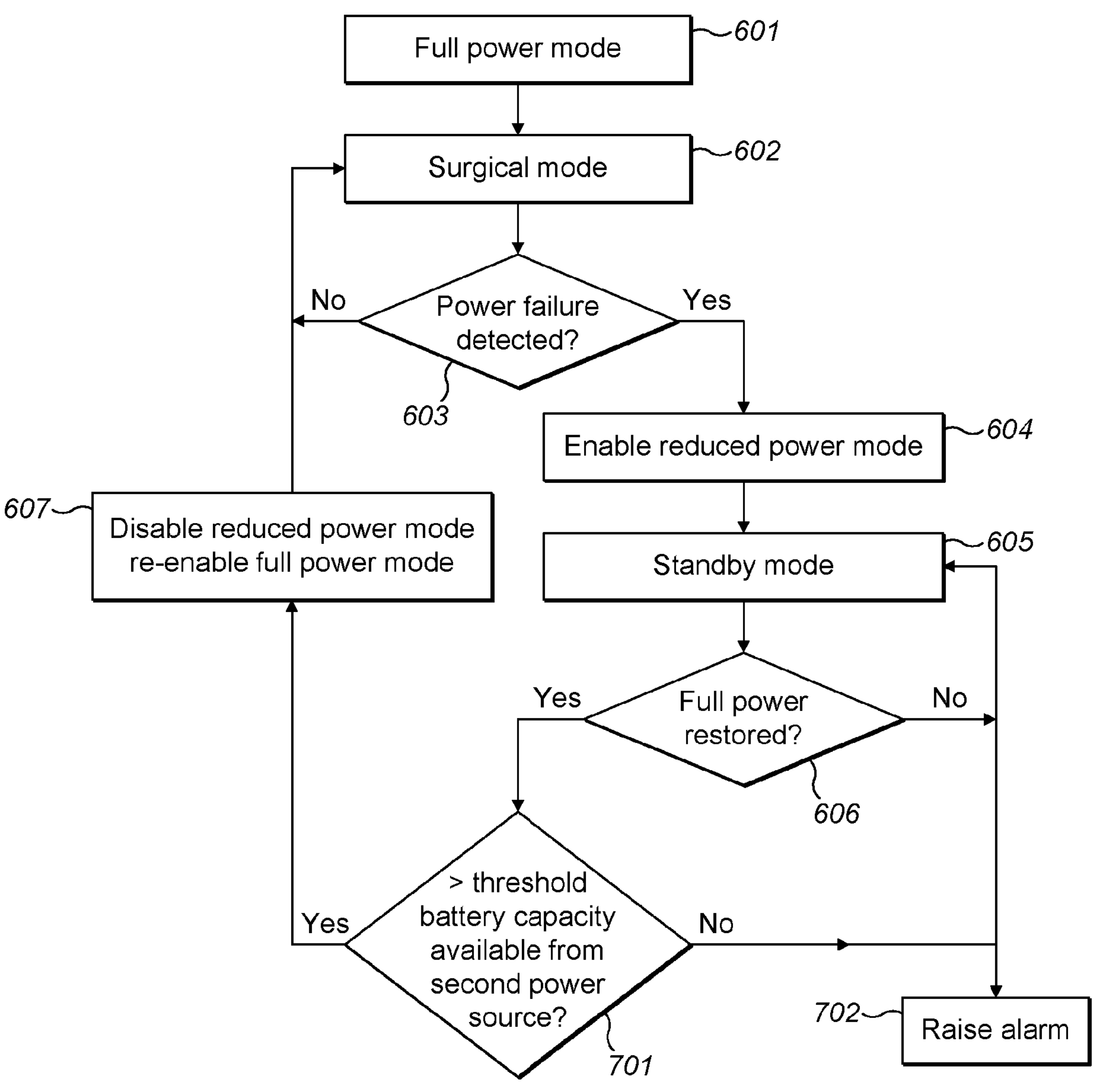

FIG. 7 illustrates a modification to the control method of FIG. 6. Steps 601 to 606 are the same as for FIG. 6. Following detecting that full power has been restored at step 606, the control system moves on to step 701. At step 701, the control system determines whether there is more than a threshold battery capacity available from the secondary power source. For example, the control system may determine whether there are more than P seconds of power available from the secondary power source. If there is more than the threshold battery capacity available from the secondary power source, then the control system proceeds to step 607, where the control system disables the reduced power mode and re-enables the full power mode. From step 607, the control system returns to the surgical mode at step 602. If there is less than the threshold battery capacity available from the secondary power source, then the control system returns to the standby mode of step 605. If there is less than the threshold battery capacity available from the secondary power source, then the control system may raise an alarm at step 702. The control system may output an alarm signal as an indicator on the surgical robot arm. For example, an audio alarm signal output from a speaker on the robot arm and/or a visual indicator such as a flashing light on the robot arm. The control system may also send an alarm signal to the remote surgeon's console. This alarm signal may be output on the surgeon's console as an audio alarm signal from a speaker on the console or a visual indicator on the surgeon's console display screen.

The control method of FIG. 7 introduces an additional safety element beyond the control method of FIG. 6. Specifically, the control method of FIG. 7 ensures that, on full power being restored, there is still sufficient battery power available to hold the surgical robot arm in position for at least P seconds before allowing the surgical robot arm to return to the surgical mode. Thus, if full power is lost again, the surgical robot arm will be held in position using power from the battery for long enough that the bedside team is able to remove the instrument from the patient's body.

In the case that the secondary power source comprises a first rechargeable battery and a second non-rechargeable battery as described above, P may be the same as T. In this case, step 701 of FIG. 7 determines whether the first rechargeable battery was fully discharged and the second non-rechargeable battery depleted to below T seconds of remaining power for holding the surgical robot arm. If so, the only battery power available is the remaining power of the second non-rechargeable battery which, if below T seconds, is not deemed long enough to be able to safely remove the surgical instrument from the patient's body. If greater than T seconds of power are remaining, then the second non-rechargeable battery and/or the first rechargeable battery have sufficient power available to enable the bedside team to safely remove the surgical instrument should another power failure of the primary power source occur.

Figure 8:
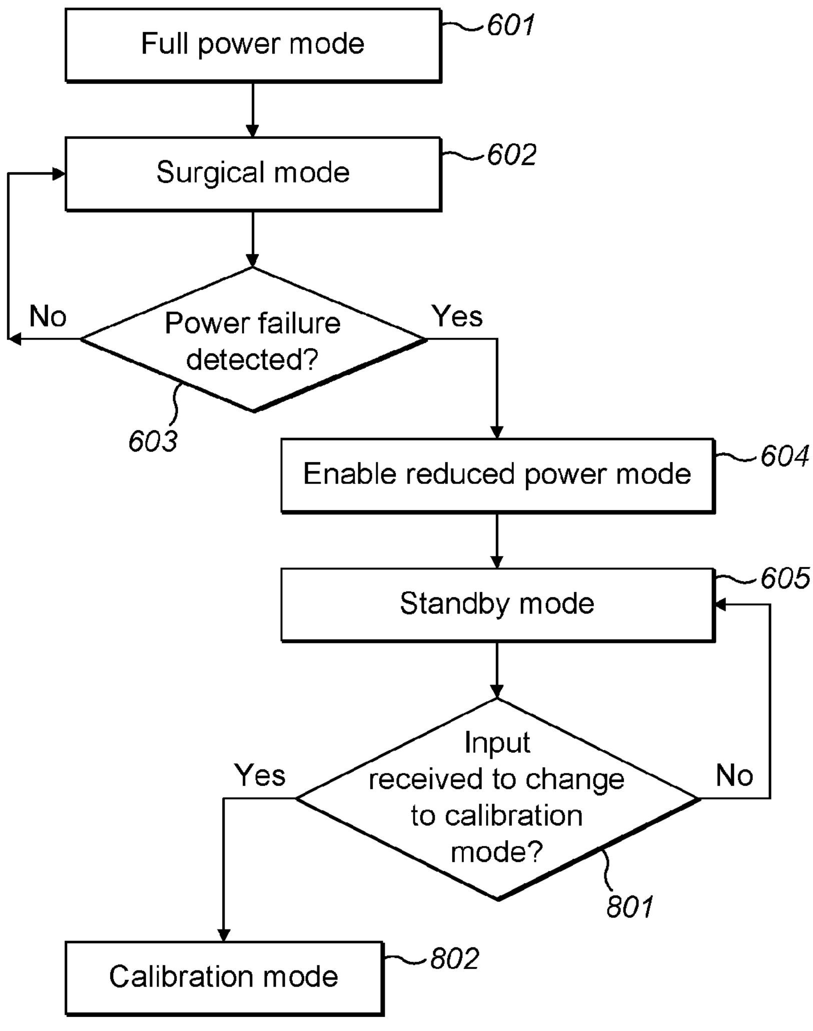

FIG. 8 illustrates a control method in which the surgical robot arm enters the standby mode 605 as described with reference to steps 601 to 605 of FIG. 6. Having entered the standby mode, at step 801, the control system determines whether a command has been received from a user input to change to a calibration mode. The user input may be an interface located on or adjacent to the surgical robot arm. For example, the interface may be located on the surgical robot arm or its support structure. The user input may be an interface located on the surgeon's console. In either case, the interface may take the form of a button, switch, slider, touch sensitive input, voice control input, eye control input or a gesture control input.

If at step 801, the control system determines that the user input has not been received, then the control system returns to the standby mode at step 605. If at step 801, the control system determines that the user input has been received, then the control method moves onto step 802. At step 802, the control system responds to the command from the user input by transitioning control of the surgical robot arm from the standby mode to the calibration mode.

The method of FIG. 8 allows the bedside team or surgeon to, upon detecting a power failure of the primary power supply, safely end the surgical robot arm's part in the surgical procedure. Upon receipt of the user input, the control system transitions the robot arm to a calibration mode in which the robot arm is driven to comply with external force applied to the robot arm. Thus, the bedside team can move the robot arm and its support structure out of the way of the patient's bed.

Figure 9:
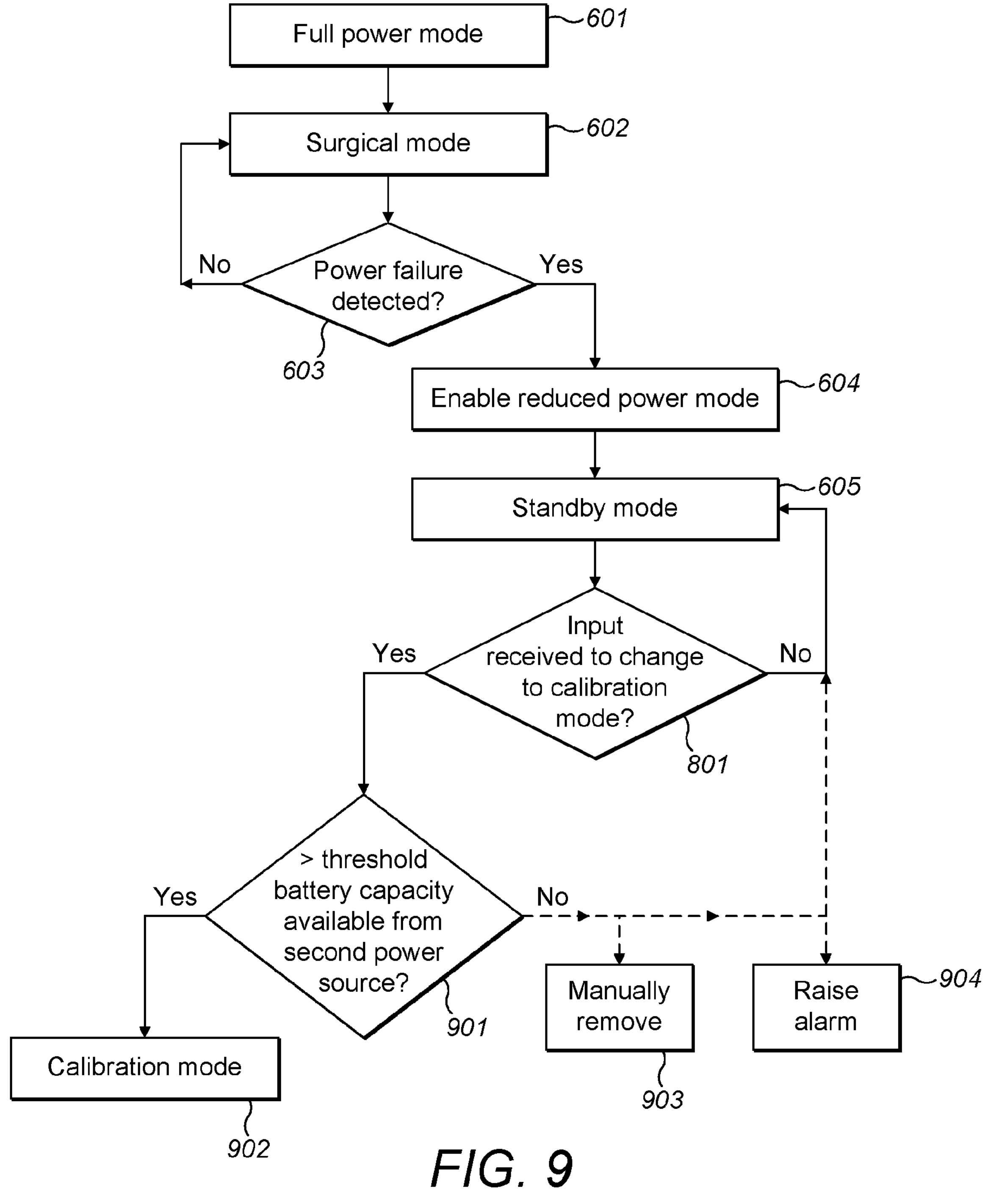

FIG. 9 illustrates a modification to the control method of FIG. 8. Steps 601 to 801 are the same as for FIG. 8. Following detecting that a command has been received from a user input to change to a calibration mode at step 801, the control method moves on to step 901. At step 901, the control system determines whether there is more than a threshold battery capacity available from the secondary power source. For example, the control system may determine whether there are more than P seconds of power available from the secondary power source. If there is more than the threshold battery capacity available from the secondary power source, then the control method proceeds to step 902. At step 902, the control system transitions control of the surgical robot arm from the standby mode to the calibration mode. If at step 901, the control system determines that there is less than the threshold battery capacity available from the secondary power source, then the control method either returns to the standby mode of step 605 or transitions to step 903, where the instrument is manually removed. If there is less than the threshold battery capacity available from the secondary power source, then the control system may raise an alarm at step 904. The control system may output an alarm signal as an indicator on the surgical robot arm as described above with reference to FIG. 7. The control system may also send an alarm signal to the remote surgeon's console as described above with reference to FIG. 7. In the case that the secondary power source comprises a first rechargeable battery and a second non-rechargeable battery as described above, P may be the same as T.

At step 903, the bedside team may manually remove the instrument by detaching the instrument from the robot arm, manually open the jaws of the instrument so as to release any tissue grasped therebetween, manually straighten the instrument by manipulating the instrument interface elements, then pull the instrument out of the patient. No tools are required to perform this function.

Figure 10:
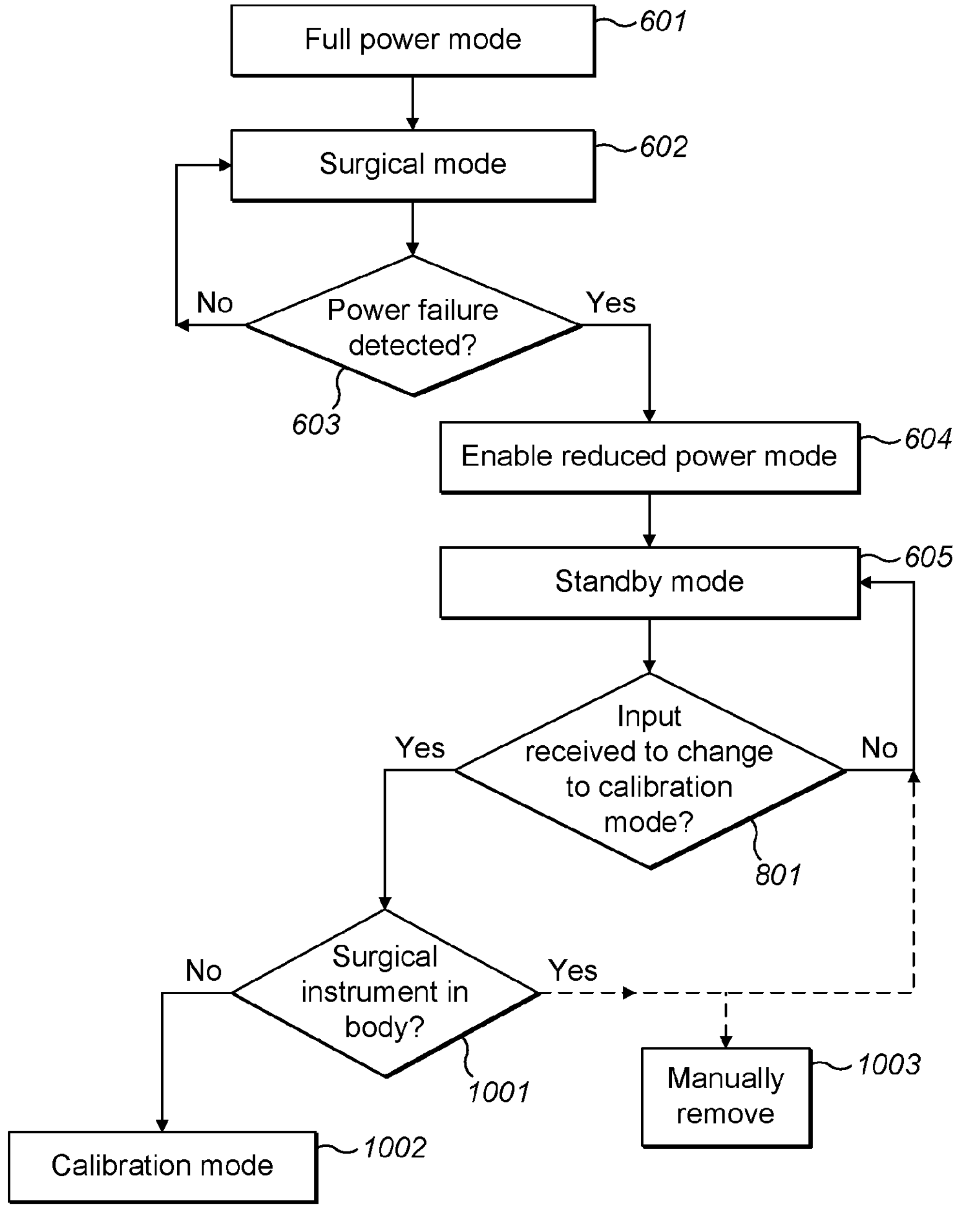

FIG. 10 illustrates a modification to the control method of FIG. 8. Steps 601 to 801 are the same as for FIG. 8. Following detecting that a command has been received from a user input to change to a calibration mode at step 801, the control method moves on to step 1001. At step 1001, the control system determines whether there is a surgical instrument attached to the surgical robot arm which is inside the patient's body. This condition is not satisfied if either: (i) there is no surgical instrument attached to the surgical robot arm, or (ii) there is a surgical instrument attached to the surgical robot arm but that surgical instrument has not been inserted in a port in the patient's body. If the control system determines there is no surgical instrument attached to the surgical robot arm that is located in the patient's body, then at step 1002, the control system transitions from the standby mode to the calibration mode. If at step 1001, the control system determines that there is a surgical instrument attached to the surgical robot arm which is located in the patient's body, then the control method moves either (i) to step 605 where the control system maintains the surgical robot arm in the standby mode, or (ii) to step 1003 where the instrument is manually removed.

Figure 11:
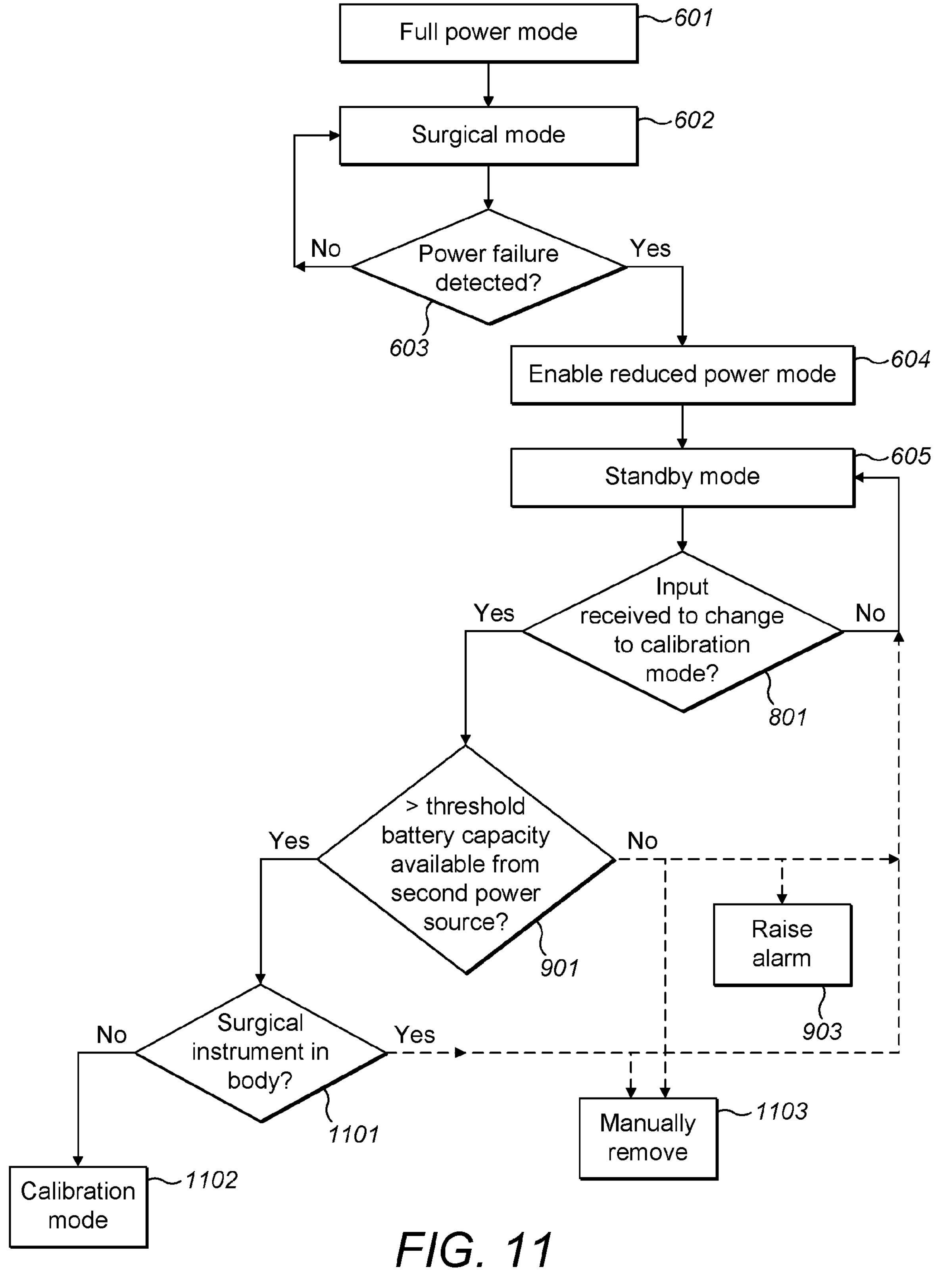

FIG. 11 illustrates a modification to the control method of FIG. 8 including both the modifications of FIGS. 9 and 10. Steps 601 to 901 are the same as for FIG. 9. If, at step 901, the control system determines that less than the threshold battery capacity is available from the second power source, then the control system either (i) maintains the surgical robot arm in standby mode 605, or (ii) at step 1103 the instrument is manually removed. In either case, an alarm may be raised at step 903.

If, however, at step 901 the control system determines that more than the threshold battery capacity is available from the second power source, then the control system moves to step 1101. At step 1101 the control system determines whether there is a surgical instrument attached to the surgical robot arm which is inside the patient's body. If the control system determines there is no surgical instrument attached to the surgical robot arm that is located in the patient's body, then at step 1102, the control system transitions from the standby mode to the calibration mode. If at step 1101, the control system determines that there is a surgical instrument attached to the surgical robot arm which is located in the patient's body, then at step 1103, the control system either (i) maintains the surgical robot arm in the standby mode at step 605, or (ii) the instrument is manually removed at step 1103.

Steps 901 and 1101 could be implemented in the order shown in FIG. 11, the other way around, or concurrently.

As with FIG. 6, although the methods of FIGS. 7, 8, 9, 10 and 11 are described with respect to the surgical mode, they apply equally to any of the operating modes of the surgical robot arm described with respect to FIG. 5, i.e. the locked mode, instrument adjust mode and instrument change mode. These modes all have the common feature that when the surgical robot arm is in them, the control system constrains motion of the surgical robot arm so as to maintain an intersection between the longitudinal axis of the shaft of the surgical instrument and the virtual pivot point.

Following a power failure, the battery supply to the surgical robot arm may become sufficiently depleted that the robot arm controller causes the surgical robot arm to enter a minimum power mode in which power is used only to maintain the position of the surgical robot arm so as to prevent the surgical instrument from advancing any further into the patient's body.

The surgical robot arm can be considered to consist of three sets of joints. Each set of joints comprises one or more joints. These three sets of joints will now be described.

For each joint of the first set of joints, there is a configuration of the surgical robot arm when the base is sat on a horizontal surface for which that joint: (i) experiences a gravitational torque or force, and (ii) movement of the joint complying with the gravitational torque or force would cause the surgical instrument attached to the surgical robot arm to advance into the patient's body towards the surgical site. To satisfy this definition, there need only be one configuration of the surgical robot arm in which the joint satisfies both the first and second condition. It may be the case that that same joint does not satisfy the first and second condition for some other configurations of the surgical robot arm. The joints of a specific surgical robot arm which satisfy this definition are dependent on the specific structure of that surgical robot arm including the sequence of joints of that surgical robot arm.

Movement of a joint of the first set of joints complying with the gravitational torque or force may cause the surgical instrument to advance through the port into the patient's body by more than a threshold distance K. For example, that threshold distance K may be in the range $0.1 \text{ cm}<K<5 \text{ cm}$. K may be in the range $1 \text{ cm}<K<3 \text{ cm}$. K may be 2 cm.

For the surgical robot arm of FIGS. 2 and 3, the first set of joints consists of the pitch joint $J_2$ 205*b*, the roll joint $J_3$ 205*c* and the pitch joint $J_4$ 205*d*. Each of these joints could move under gravity and thereby cause the instrument to advance into the patient's body. $J_2$ is a pitch joint with a horizontal axis of rotation when the base of the surgical robot arm is on a horizontal surface. Thus, gravity causes $J_2$ to rotate about its axis. $J_3$ is a roll joint with an axis of rotation along the $J_2$-$J_4$ arm link. The direction of the $J_2$-$J_4$ arm link varies with the pose of the surgical robot arm. If the $J_2$-$J_4$ arm link is vertical, then $J_3$ does not experience a gravitational torque. However, if $J_2$-$J_4$ arm link lies along any non-vertical direction, then $J_3$ experiences a torque under gravity. $J_4$ is a pitch joint whose rotation axis varies with robot arm pose. Unless the robot arm is in a completely folded position, the weight of the robot arm from $J_4$ to the terminal end exerts a force on $J_4$ under gravity.

For each joint of the second set of joints, there is no configuration of the surgical robot arm when the base is sat on a horizontal surface for which that joint experiences a gravitational torque or force. The joints of a specific surgical robot arm which satisfy this definition are dependent on the specific structure of that surgical robot arm including the sequence of joints of that surgical robot arm.

For the surgical robot arm of FIGS. 2 and 3, the second set of joints are adjacent to the base of the surgical robot arm. The second set of joints are between the base and the first set of joints. The second set of joints consists of the roll joint $J_1$ 205*a*. This roll joint has a vertical axis of rotation when the base of the surgical robot arm is on a horizontal surface. Thus, this roll joint does not move about its axis under the force of gravity.

For each joint of the third set of joints, there is no configuration of the surgical robot arm when the base is sat on a horizontal surface for which movement of that joint alone under gravity would cause the surgical instrument attached to the surgical robot arm to advance through the port towards the surgical site in the patient's body. The joints of a specific surgical robot arm which satisfy this definition are dependent on the specific structure of that surgical robot arm including the sequence of joints of that surgical robot arm.

Movement of a joint of the third set of joints alone under gravity may cause substantially no advancement of the instrument into the patient's body. Movement of a joint of the third set of joints alone under gravity may cause an insignificant advancement of the instrument into the patient's body. Movement of a joint of the third set of joints complying with the gravitational torque or force may cause the surgical instrument to advance into the patient's body by less than a threshold distance L. For example, that threshold distance L may be in the range $0 \text{ cm}<L<2 \text{ cm}$. L may be in the range $0 \text{ cm}<L<0.2 \text{ cm}$. L may be 2 cm.

The port or the patient's abdomen may partially support the weight of the instrument, thereby preventing the instrument from inserting further into the patient's body due to movement of a joint of the third set of joints under gravity alone. The instrument may not move further into the patient's body by more than a distance permitted by the elasticity of the patient's abdomen due to movement alone of one joint of the third set of joints under gravity.

For the surgical robot arm of FIGS. 2 and 3, the third set of joints are successive joints adjacent to the terminal end of the surgical robot arm. The third set of joints are between the terminal end of the surgical robot arm and the first set of joints. The third set of joints consists of the roll joint $J_5$ 205*e*, the pitch joint $J_6$ 205*f*, the yaw joint $J_7$ 205$_g$ and the roll joint is 205*h*. $J_5$ is a roll joint which has an axis of rotation along the $J_4$-$J_6$/$J_7$ arm link. Thus, is contributes to the rotation of the wrist only. Movement of $J_5$ cannot cause the instrument to be inserted further into the patient's body. The weight of the robot arm from $J_5$ to the terminal end does not exert a torque on the joint $J_5$. $J_6$ and $J_7$ have coincident and perpendicular axes of rotation which are coincident with the definition of the wrist position (see above). Movement of $J_6$ or $J_7$ cannot cause the instrument to be inserted further into the patient's body. The weight of the wrist does not exert a torque on either joint $J_6$ or $J_7$. $J_8$ is a roll joint having an axis of rotation along the longitudinal axis of the instrument's shaft. Rotation of $J_8$ about its axis cannot cause the instrument to be inserted further into the patient's body. The weight of the wrist does not exert a torque on $J_8$.

Figure 12:
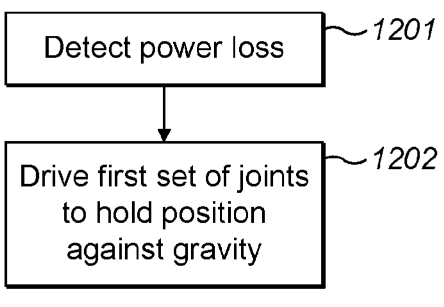

FIG. 12 illustrates a method carried out by the robot arm controller. At step 1201, the robot arm controller detects a power loss. The power loss may be detected in any suitable way, such as those described above. As another example, power loss may be detected through use of a sensor which detects the physical connection of the power cable to the robot arm or its supporting structure. On detecting a lack of physical connection of the power cable, a power loss is detected. In response to this, at step 1202, the robot arm controller drives the first set of joints to hold the position of each joint of the first set of joints against gravity. The robot arm controller only drives the first set of joints to hold their positions against gravity. The robot arm controller does not drive the second set of joints or the third set of joints to hold their positions against gravity. More specifically, the robot arm controller sends control signals to the joint controller(s) of the first set of joints to electrically brake the first set of joints. The joint controller(s) respond to the control signals from the robot arm controller by controlling the joint motors for the joints of the first set of joints to brake each joint of the first set of joints, and thereby hold the position of each of the joints against gravity. The robot arm controller does not send control signals to the joint controllers of the second and third sets of joints commanding them to electrically brake the second and third sets of joints.

Suitably, the control method of FIG. 12 is implemented when complete power failure is imminent. The robot arm controller responds to this situation by minimising power usage as described with reference to FIG. 12 by only actively driving those joints of the surgical robot arm to hold their position against gravity which are critical from a safety perspective. The safety critical joints are those ones which: (i) would move under gravity if they were not being held in position by electrical braking, and (ii) such movement under gravity could cause the instrument to advance further into the patient's body. Other joints may cause rotation of the surgical instrument within the patient's body when not being actively driven to hold their position against gravity, but not further advancement of the surgical instrument into the patient's body, and hence they are not safety critical joints.

In the surgical robot arm described with reference to FIGS. 2 and 3, joints $J_2$, $J_3$ and $J_4$ droop under gravity in at least some configurations of the surgical robot arm when the base of the surgical robot arm is on a horizontal surface, and that drooping could cause the instrument attached to the surgical robot arm to advance further into the patient's body. Thus, joints $J_2$, $J_3$ and $J_4$ are the safety critical joints in this example, which are electrically braked so as to maintain their position against gravity in step 1202 of FIG. 12. In addition to preventing the instrument from moving further into the patient's body, electrically braking joints $J_2$, $J_3$ and $J_4$ also prevents the wrist of the surgical robot arm from moving under gravity. This prevents the instrument from pivoting about the virtual pivot point which could cause movement of the instrument in the patient's body.

By only applying the minimum power to the surgical robot arm to prevent the surgical instrument from advancing further into the patient's body, the remaining battery life is extended for as long as possible. Step 1202 of FIG. 12 may enable the safety critical joints to be electrically braked for at least R seconds. For example, 30 seconds<R<120 seconds. R may be, for example, 60 seconds. During this time, the bedside team can act to safely withdraw the surgical instrument from the patient's body.

The degree of power loss that triggers the robot arm controller to detect power loss in step 1201 of FIG. 12 is implementation specific. For example, the robot arm controller may be configured to detect power loss if it determines that the remaining battery life of the second power source has dropped below a threshold value W. That threshold value W may be in the range 30 seconds<W<5 minutes. That threshold value W may be in the range 60 seconds<W<2 minutes. W may be 60 seconds.

As another example, the robot arm controller may be configured to detect power loss if it determines that the remaining power capacity of the second power source has dropped below a threshold power capacity.

As another example, the robot arm controller may be configured to detect power loss if it determines that the voltage or current supplied by the second power source falls below a threshold value V. For example, V may be in the range 6V<V<11V.

As another example, if the secondary power source comprises a first battery and a second battery, the robot arm controller may be configured to detect power loss on determining that the first battery is depleted. The robot arm controller may detect depletion of the first battery when the voltage or current supplied by that first battery falls below a threshold value U. For example, U may be in the range 8V<U<15V. The robot arm controller may comprise watchdog circuitry which monitors the status of the power sources of the surgical robot arm. Suitably, the robot arm controller receives power inputs from each of the primary power source, the first battery and the second battery. The robot arm controller controls which power source supplies power to the surgical robot arm. On detecting a loss of power from the first battery, the robot arm controller switches from connecting the power input from the first battery to the surgical robot arm, to connecting the power input from the second battery to the surgical robot arm. The robot arm controller may also prevent communications between the processor of the robot arm controller and the remainder of the surgical robot arm. For example, the robot arm controller may prevent communications being sent commanding the joint controllers to move the joints of the surgical robot arm according to movements of the surgeon input device. The robot arm controller causes the surgical robot arm to enter a fault locked state in which holding driving signals are sent to the joint controllers driving the critical joints only to drive those critical joints to counteract gravity. If the second battery is a non-rechargeable battery, then it may need to be replaced following use to hold the robot arm against gravity in step 1201.

The robot arm controller may only be configured to detect the power loss at step 1201 of FIG. 12 if the robot arm controller has already detected a loss of power from the primary power supply.

Once the robot arm controller has implemented the control method of FIG. 12, it may be configured to not transition the surgical robot arm to any of the operating modes in FIG. 5, even if power from the primary source is restored. Instead, the surgical robot arm is powered down for maintenance before being used again.

The robot described herein could be for purposes other than surgery. For example, the port could be an inspection port in a manufactured article such as a car engine and the robot could control a viewing tool for viewing inside the engine.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical robot comprising:

a surgical robot arm comprising:

a series of joints extending from a base to a terminal end for attaching to a surgical instrument for inserting through a port into a patient's body to a surgical site, the series of joints comprising a first set of joints, wherein for each joint of the first set of joints, there is a configuration of the surgical robot arm for which that joint experiences a gravitational torque or force and a movement of that joint complying with the gravitational torque or force would cause the surgical instrument to advance into the patient's body towards the surgical site;

joint motors for driving the series of joints; and a surgical robot arm controller configured to send drive signals to drive the joint motors, wherein the surgical robot arm controller is configured to, in response to detecting a power loss from a first power source, send drive signals to drive the joint motors using a second power source so as to hold the position of each joint of the first set of joints against gravity, thereby preventing the surgical instrument from advancing into the patient's body towards the surgical site due to movement of one or more joints of the first set of joints under gravity;

wherein the series of joints comprises at least one other joint which is not in the first set of joints and for which it is not the case that there is a configuration of the surgical robot arm for which that joint experiences a gravitational torque or force which would result in movement of that joint that would cause the surgical instrument to advance into the patient's body towards the surgical site, and wherein the surgical robot arm controller is configured to, in response to detecting said power loss, not send drive signals to drive the at least one or more joint motors so as to hold the position of each of said at least one other joint against gravity.

2. A surgical robot as claimed in claim 1, wherein the series of joints comprises a second set of joints, wherein for each joint of the second set of joints, there is no configuration of the surgical robot arm for which that joint experiences a gravitational torque or force.

3. A surgical robot as claimed in claim 2, wherein of the first and second sets of joints, the surgical robot arm controller is configured to only send drive signals to drive the joint motors so as to hold the position of the first set of joints against gravity in response to detecting a power loss.

4. A surgical robot as claimed in claim 2, wherein the second set of joints are adjacent to the base of the surgical robot arm.

5. A surgical robot as claimed in claim 2, wherein the second set of joints are between the base of the surgical robot arm and the first set of joints.

6. A surgical robot as claimed in claim 1, wherein the series of joints comprises a third set of joints, wherein for each joint of the third set of joints, there is a configuration of the surgical robot arm for which that joint experiences a gravitational torque or force but no movement of that joint alone complying with the gravitational torque or force would cause the surgical instrument to advance through the port towards the surgical site.

7. A surgical robot as claimed in claim 6, wherein of the first and third sets of joints, the surgical robot arm controller is configured to only send drive signals to drive the joint motors so as to hold the position of the first set of joints against gravity in response to detecting a power loss.

8. A surgical robot as claimed in claim 2, wherein the series of joints comprises a third set of joints, wherein for each joint of the third set of joints, there is a configuration of the surgical robot arm for which that joint experiences a gravitational torque or force but no movement of that joint alone complying with the gravitational torque or force would cause the surgical instrument to advance through the port towards the surgical site and wherein of the first, second and third sets of joints, the robot arm controller is configured to only send drive signals to drive the joint motors so as to hold the position of the first set of joints against gravity in response to detecting a power loss.

9. A surgical robot as claimed in claim 6, wherein the third set of joints are successive joints adjacent to the terminal end of the surgical robot arm and are located between the terminal end of the surgical robot arm and the first set of joints.

10. A surgical robot as claimed in claim 1, wherein the series of joints consist of in order from the base of the surgical robot arm: a first roll joint, a first pitch joint, a second roll joint, a second pitch joint, a third roll joint, a third pitch joint, a first yaw joint, and a fourth roll joint.

11. A surgical robot as claimed in claim 10, wherein the first set of joints consists of the first pitch joint, the second roll joint and the second pitch joint.

12. A surgical robot as claimed in claim 10, wherein the series of joints comprises a third set of joints, wherein for each joint of the third set of joints, there is a configuration of the surgical robot arm for which that joint experiences a gravitational torque or force but no movement of that joint alone complying with the gravitational torque or force would cause the surgical instrument to advance through the port towards the surgical site, and wherein the third set of joints consists of the third roll joint, the third pitch joint, the first yaw joint, and the fourth roll joint.

13. A surgical robot as claimed in claim 1, wherein the first power source is a mains electrical supply and the second power source is a first battery supply, and wherein the detected power loss is loss of power to the surgical robot arm from the mains electrical supply.

14. A surgical robot as claimed in claim 1, wherein the first power source is a first battery supply and the second power source is a second battery supply, and wherein the detected power loss is loss of power to the surgical robot arm from the first battery supply.

15. A surgical robot as claimed in claim 14, wherein the surgical robot arm controller is configured to detect a loss of power to the surgical robot arm from a primary power supply prior to detecting the loss of power to the surgical robot arm from the first battery supply.

16. A surgical robot as claimed in claim 15, wherein the surgical robot arm controller is configured to, prior to detecting the loss of power from the primary power supply, control the surgical robot arm and attached surgical instrument to move according to inputs received from a remote surgeon input device.

17. A surgical robot as claimed in claim 1, wherein the surgical robot arm controller is integrated into the surgical robot arm.

18. A surgical robot as claimed in claim 1, wherein the surgical robot arm is mounted on a support structure, and the surgical robot arm controller is integrated into the support structure.

19. A control method for controlling a surgical robot arm comprising a series of joints extending from a base to a terminal end for attaching to a surgical instrument for inserting into a patient's body to a surgical site, the series of joints comprising a first set of joints, wherein for each joint of the first set of joints, there is a configuration of the surgical robot arm for which that joint experiences a gravitational torque or force and a movement of that joint complying with the gravitational torque or force would cause the surgical instrument to advance into the patient's body towards the surgical site, the surgical robot arm further comprising joint motors for driving the series of joints, the method comprising:

sending, in response to detecting a power loss from a first power source, drive signals to drive the joint motors using a second power source so as to hold the position of each joint of the first set of joints against gravity, thereby preventing the surgical instrument from advancing into the patient's body towards the surgical site due to movement of one or more joints of the first set of joints under gravity;

wherein the series of joints comprises at least one other joint which is not in the first set of joints and for which it is not the case that there is a configuration of the surgical robot arm for which that joint experiences a gravitational torque or force which would result in movement of that joint that would cause the surgical instrument to advance into the patient's body towards the surgical site, and wherein the surgical robot arm controller is configured to, in response to detecting said power loss, not send drive signals to drive the at least one or more joint motors so as to hold the position of each of said at least one other joint against gravity.

* * * * *